(12) United States Patent
Slayton

(10) Patent No.: US 10,765,851 B2
(45) Date of Patent: Sep. 8, 2020

(54) METHODS AND SYSTEMS FOR MATERIAL TRANSPORT ACROSS AN IMPERMEABLE OR SEMI-PERMEABLE MEMBRANE VIA ARTIFICIALLY CREATED MICROCHANNELS

(71) Applicant: Guided Therapy Systems, LLC, Mesa, AZ (US)

(72) Inventor: Michael H. Slayton, Tempe, AZ (US)

(73) Assignee: Guided Therapy Systems LLC, Scottsdale, AZ (US)

( * ) Notice: Subject to any disclaimer, the term of this patent is extended or adjusted under 35 U.S.C. 154(b) by 309 days.

(21) Appl. No.: 15/059,773

(22) Filed: Mar. 3, 2016

(65) Prior Publication Data

US 2016/0256675 A1    Sep. 8, 2016

Related U.S. Application Data

(60) Provisional application No. 62/127,720, filed on Mar. 3, 2015, provisional application No. 62/127,715, filed on Mar. 3, 2015.

(51) Int. Cl.
*A61M 37/00* (2006.01)
*A61K 9/00* (2006.01)
(Continued)

(52) U.S. Cl.
CPC ....... *A61M 37/0092* (2013.01); *A61K 9/0021* (2013.01); *A61K 31/047* (2013.01); *A61K 31/07* (2013.01); *A61K 31/167* (2013.01); *A61K 31/192* (2013.01); *A61K 31/203* (2013.01); *A61K 31/4174* (2013.01); *A61K 31/496* (2013.01); *A61K 31/573* (2013.01);
(Continued)

(58) Field of Classification Search
CPC ........ A61K 9/0021; A61M 2037/0023; A61M 2037/0053; A61M 2037/0061; A61M 2205/051; A61M 37/0015; A61M 37/0092
See application file for complete search history.

(56) References Cited

U.S. PATENT DOCUMENTS 7,591,996 B2 * 9/2009 Hwang ............... A61K 38/363
424/9.1
2006/0253078 A1 * 11/2006 Wu ................... A61M 37/0015
604/173
(Continued)

OTHER PUBLICATIONS

Campbell, et al., "Systemic absorption of topical lidocaine in normal volunteers, patients with post-herpetic heuralgia, and patients with acute herpes zoster." J. Pharm. Sci. 91(5), pp. 1343-1350 (May 2002).
(Continued)

*Primary Examiner* — Kevin C Sirmons
*Assistant Examiner* — Tezita Z Watts
(74) *Attorney, Agent, or Firm* — Quarles & Brady LLP

(57) ABSTRACT

Systems and methods are disclosed for transporting a transport target across a membrane that is impermeable or semi-permeable to the transport target via artificially created microchannels or through hypodermic microneedles. The transport target can be a medicant and the membrane can be a stratum corneum layer of skin. The transport is enhanced by the application of ultrasound energy having a high peak intensity, which generates an inertial cavitation effect, an acoustic streaming effect, or both.

14 Claims, 16 Drawing Sheets

(51) Int. Cl.
    *A61N 5/06*     (2006.01)
    *A61K 31/047*     (2006.01)
    *A61K 31/192*     (2006.01)
    *A61K 31/4174*     (2006.01)
    *A61K 31/203*     (2006.01)
    *A61K 31/496*     (2006.01)
    *A61K 31/573*     (2006.01)
    *A61K 31/167*     (2006.01)
    *A61K 31/07*     (2006.01)

(52) U.S. Cl.
    CPC ..... *A61N 5/062* (2013.01); *A61M 2037/0023* (2013.01); *A61M 2037/0061* (2013.01); *A61M 2205/051* (2013.01); *A61N 5/0603* (2013.01); *A61N 5/0616* (2013.01); *A61N 2005/061* (2013.01); *A61N 2005/0604* (2013.01); *A61N 2005/0609* (2013.01)

(56) References Cited

U.S. PATENT DOCUMENTS

2008/0281255 A1* 11/2008 Slayton ............. A61M 37/0092 604/22
2011/0245776 A1* 10/2011 Kendall ............... A61B 17/205 604/173
2013/0096471 A1* 4/2013 Slayton ............. A61M 37/0092 601/3

OTHER PUBLICATIONS

Church CC, et al. "A theroretical study of inertial cavitation from acoustic radiation force impulse imaging and implications for the MI," Ultrasound in Med. & Biol., vol. 41, No. 2, pp. 472-485 (2015).

* cited by examiner

METHODS AND SYSTEMS FOR MATERIAL TRANSPORT ACROSS AN IMPERMEABLE OR SEMI-PERMEABLE MEMBRANE VIA ARTIFICIALLY CREATED MICROCHANNELS

CROSS-REFERENCE TO RELATED APPLICATIONS

This application is related to, claims priority to, and incorporated by references herein for all purposes U.S. Provisional Patent Application No. 62/127,715, filed Mar. 3, 2015, and U.S. Provisional Patent Application No. 62/127,720, filed Mar. 3, 2015.

BACKGROUND

Trandermal delivery of medicants is limited primarily to the difficult-to-penetrate nature of the stratum corneum layer of skin. The stratum corneum layer forms a barrier that keeps moisture in and keeps practically everything else out. Accordingly, attempts to topically apply a medicant and deliver the medicant across the stratum corneum layer to tissue located beneath it must overcome this barrier property in order to be effect.

The bioavailability of topically applied medicants is typically very low. For example, the bioavailability of topically applied lidocaine is approximately 3%. See, Campbell, et al. J. Pharm. Sci. 91(5), pp. 1343-50 (May 2002). In other words, more than 30 times the desired amount of lidocaine needs to be applied topically for the desired effect. In the case of an expensive medicant or a medicant having various side effects, it is undesirable to require application of such an excess of medicant in order to have the desired effect.

Low-frequency sonophoresis is a known method for enhancing transdermal drug delivery. However, these existing methods employ low-frequencies, low peak intensities, require long application times, or some combination of these to achieve improved transdermal drug delivery.

Microchannels can provide fluid communication between one side of a semi-permeable or impermeable membrane and an opposite side. However, transport of a transport target through a microchannel is slow and limited by diffusion and capillary forces.

Accordingly, a need exists for new systems and methods that overcome the aforementioned shortcomings.

SUMMARY

The present disclosure overcomes the aforementioned drawbacks by presenting systems and methods for material transport across an impermeable or semi-permeable membrane via artificially created microchannels.

In one aspect, this disclosure provides a method for transporting a medicant across a stratum corneum layer of a skin and into a dermis layer of the skin. The method can include: contacting a top surface of the stratum corneum layer with the medicant; creating a microchannel in the membrane, the microchannel providing fluid communication between the top surface of the stratum corneum layer and an epidermis layer of the skin; directing a first acoustic energy field from an acoustic energy source or a first photon-based energy field from a photon-based energy source to the medicant, thereby driving the transport target through the microchannel and into the epidermis layer of the skin; and subsequent to the medicant being driven into the epidermis layer of the skin, applying a second acoustic energy field to the medicant, thereby driving the medicant from the epidermis layer of the skin and into the dermis layer of the skin.

In another aspect, this disclosure provides a method for transporting a medicant across a stratum corneum layer of a skin and into a dermis layer of the skin. The method can include: inserting a hypodermic microneedle into the stratum corneum layer from a top surface, an interior of the hypodermic microneedle in fluid communication with a reservoir containing the medicant, the hypodermic microneedle providing fluid communication between the reservoir and the epidermis layer of the skin; directing a first acoustic energy field from an acoustic energy source or a first photon-based energy field from a photon-based energy source to the medicant, thereby driving the medicant through the microneedle and into the epidermis layer of the skin; and subsequent to the medicant being driven into the epidermis layer of the skin, applying a second acoustic energy field to the medicant, thereby driving the medicant from the epidermis layer of the skin and into the dermis layer of the skin.

In yet another aspect, this disclosure provides a method for transporting a transport target across a membrane that is semi-permeable or impermeable to a transport target. The method can include: contacting a top surface of the membrane with the transport target; creating a microchannel in the membrane, the microchannel providing fluid communication between the top surface of the stratum corneum layer and an epidermis layer of the skin; directing a first acoustic energy field from an acoustic energy source or a first photon-based energy field from a photon-based energy source to the medicant, thereby driving the transport target through the microchannel and into the epidermis layer of the skin; and subsequent to the medicant being driven into the epidermis layer of the skin, applying a second acoustic energy field to the medicant, thereby driving the medicant from the epidermis layer of the skin and into the dermis layer of the skin.

In a further aspect, this disclosure provides a method for transporting a transport target across a membrane that is semi-permeable or impermeable to a transport target. The method can include: inserting a hollow microneedle into the membrane from a top membrane surface, an interior of the hollow microneedle in fluid communication with a reservoir containing the transport target, the membrane having a bottom membrane surface opposite the top membrane surface, the hollow microneedle providing fluid communication between the reservoir and a first material layer contacting the bottom membrane surface; and directing a first acoustic energy field from an acoustic energy source or a first photon-based energy field from a photon-based energy source to the transport target, thereby driving the transport target through the microneedle and into the first material layer.

In yet another aspect, this disclosure provides a system for delivering a transport target across a membrane from a top membrane surface to a first material layer that is adjacent to the membrane and opposite the top membrane surface. The membrane can be semi-permeable or impermeable to the transport target. The system can include a standoff, a probe housing, a power supply, and a control module. The standoff can include the transport target. The standoff can be adapted to be positioned between the probe housing and the top membrane surface. The standoff can include a bottom standoff surface configured to engage the top membrane surface and including one or more pores. The probe housing can include a microchannel probe and an ultrasound energy source. The microchannel probe can be configured to create a microchannel in the membrane. The ultrasound energy source can be configured to deliver an acoustic energy field to the transport target, thereby driving the transport target from the standoff, through the one or more pores, through the microchannel, and into the first material layer. The power supply can be configured to power the ultrasound energy source. The control module can be configured to control the ultrasound energy source.

In a further aspect, this disclosure provide a system for delivering a transport target across a membrane from a top membrane surface to a first material layer that is adjacent to the membrane and opposite the top membrane surface. The membrane can be semi-permeable or impermeable to the transport target. The system can include a standoff, an ultrasound energy source, a power supply, and a control module. The standoff can include the transport target. The standoff can be adapted to be positioned between a probe housing and the top membrane surface. The standoff can include a bottom standoff surface configured to engage the top membrane surface and including a hollow microneedle configured to puncture the membrane and provide fluid communication between the standoff and the first material layer. The ultrasound energy source can be configured to deliver an acoustic energy field to the transport target, thereby driving the transport target from the standoff, through the hollow microneedle, and into the first material layer. The power supply can be configured to power the ultrasound energy source. The control module can be configured to control the ultrasound energy source.

The foregoing and other aspects and advantage of the invention will appear from the following description. In the description, reference is made to the accompanying drawings which form a part hereof, and in which there is shown by way of illustration a preferred aspect of the disclosure. Such aspect does not necessarily represent the full scope of the disclosure, however, and reference is made therefore to the claims and herein for interpreting the scope of the disclosure.

DETAILED DESCRIPTION

Figure 1A:
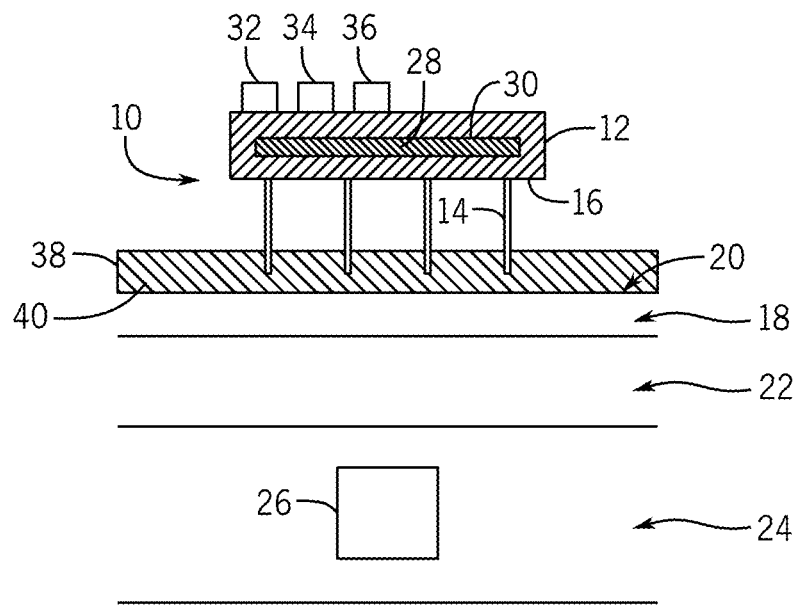
FIG. 1A illustrates a delivery system and a first stage of a method of its use, according to one aspect of the present disclosure.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices, and methods relating to improved ultrasound treatment efficiency and operation are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

When describing microneedles herein, it is contemplated that the disclosure encompasses solid microneedles, hollow microneedles, and hypodermic microneedles, unless the context clearly dictates otherwise.

This disclosure provides methods and systems for enhancing delivery of a transport target, such as a medicant, across a semi-permeable or impermeable membrane, such as the stratum corneum layer of skin, and into a first medium layer, such as an epidermis layer of skin. The systems and methods can also facilitate movement of the transfer target deeper into the first medium layer or into a second medium layer, such as the dermis layer of the skin, or a subsequent layer, such as subcutaneous tissue.

As will be described with respect to FIGS. 1A, 1B, 1C, and 1D, a delivery can include an ultrasound probe 12 and one or more microneedles 14 projecting from a bottom or other ultrasound probe surface 16. The delivery system 10 can be positioned atop and coupled to an impermeable or semi-permeable membrane 18 having a top membrane surface 20. The membrane 18 can be located above a first material layer 22 and an optional second material layer 24. One or more optional subsequent material layers can also be present beneath the second material layer 26. A region of interest 26 can be any contiguous location within the illustrated first material layer 22 or second material layer 24, or within an unillustrated subsequent material layer. The ultrasound probe 12 can include an ultrasound source 28, which can include one or more transducers 30. The ultrasound source 28 and transducers 30 can be any of a variety of ultrasound sources or transducers known to one of skill in the art or developed in the future to be suitable for producing the ultrasound characteristics described herein. The one or more transducers 30 can each independently be a single transduction element, an array of transduction elements, or a group of arrays of transduction elements. The ultrasound probe 12 can be coupled to a power supply 32 and electronics 34 sufficient for the operation of an ultrasound system. The power supply 32 can be any power supply known to one of skill in the art to be suitable for powering an ultrasound probe. The electronics 34 can be those electronics known to one of skill in the art to be suitable for operating an ultrasound probe. The ultrasound probe 12 can be coupled to a control module 36 adapted to control the emission of ultrasound from the ultrasound probe 12. The control module 36 can be a control module or controller known to one of skill in the art to be suitable for controlling the emission characteristics of an ultrasound probe 12.

Examples of suitable power supplies 32 can include, but are not limited to, one or more direct current (DC) power supplies, single-use or rechargeable batteries, or other power supplies configured to provide electrical energy to the ultrasound probe 12, including to the ultrasound source 28, transducers 30, electronics 34, control modules 36, or any other aspect of the ultrasound probe 12 that requires electrical energy. Associated sensors for monitoring the performance of the power supplies 32 are contemplated, such as current sensors, power sensors, and the like.

Examples of suitable electronics 34 can include, but are not limited to, amplifiers or drivers, such as multi-channel or single channel power amplifiers or drivers; power converters configured to adjust voltages; open-loop feedback systems; closed-loop feedback systems; filters, such as harmonic filters or matching filters; and the like.

Control modules 36 can include components suitable for controlling the emission characteristics of the ultrasound probe 12, including but not limited to, a computing system adapted to control the ultrasound probe 12; timing circuits; software and algorithms to provide control and user interfacing; input controls, such as switches, buttons, touchscreens, and the like; outputs, such as lighting or audio signals or displays; storage elements, such as memory to store calibration and usage data; and the like.

The delivery system 10 can also include sensors suitable for measuring certain aspects of the delivery system 10. Examples of sensors include, but are not limited to, temperature sensors, motion sensors, location sensors, coupling sensors, such as capacitive or acoustic coupling sensors, and the like.

The transducer 30 can be configured as a spherically-focused single element transducer, an annular/multi-element transducer, an annular array having an imaging region, a line-focused single-element transducer, a one-dimensional linear array, a one-dimensional curved linear array, a two-dimensional array with a mechanical focus, a convex lens focus, a concave lens focus, a compound lens focus, or a multiple lens focus, a two-dimensional planar array, or other transducer arrangements suitable for producing the ultrasound energy described herein and corresponding effects.

Referring to FIG. 1A, the delivery system 10 is illustrated positioned above the top membrane surface 20. A layer of coupling medium 38 is positioned atop the top membrane surface 20. The coupling medium 38 can include a transport target 40. In some aspects, the transport target 40 can be dispersed or dissolved in the coupling medium 38. In some aspects, the coupling medium 38 itself can be the transport target 40.

Figure 1B:
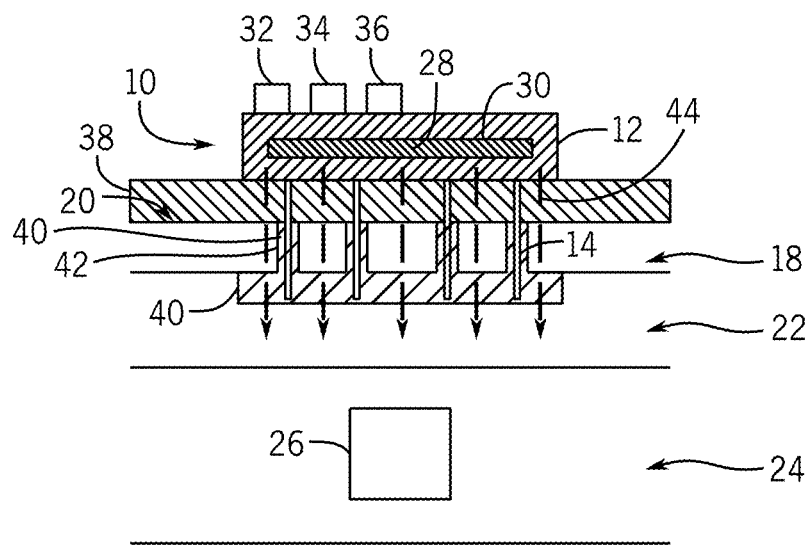
FIG. 1B illustrates a delivery system and a second stage of a method of its use, according to one aspect of the present disclosure.

Referring to FIG. 1B, the arrangement illustrated in FIG. 1A is illustrated after the delivery system 10 has been coupled to the top membrane surface 20, and the microneedles 14 have punctured the membrane 18, thereby creating microchannels 42 in the membrane 18, and the ultrasound probe 12 has begun emitting a first ultrasound energy field 44. The microchannels 42 extend over the full depth of the membrane 18. The first acoustic energy field 44 can penetrate at least through the membrane 18 and at least partially into the first material layer 22. In response to the first acoustic energy field 44, the transport target 40 can be driven from above the top membrane surface 20, into or through the microchannels 42, and into the first material layer 22.

It should be appreciated that there exist intermediate states between the state of the arrangement in FIG. 1A and that illustrated in FIG. 1B, where the delivery system 10 is positioned between the illustrated positions. There also exist intermediate states where the first acoustic energy field 44 penetrates only partially into the membrane 18, or penetrates throughout the membrane 18, but not into the first material layer 22, or penetrates throughout the membrane 18 and partially into the first material layer 22 to a depth different than that illustrated. In similar intermediate states, the transport target 40 can penetrate only partially into the microchannels 42, or penetrates throughout the microchannels 42, but not into the first material layer 22, or penetrates throughout the microchannels 42 and partially into the first material layer 22 to a depth different than that illustrated.

Figure 1C:
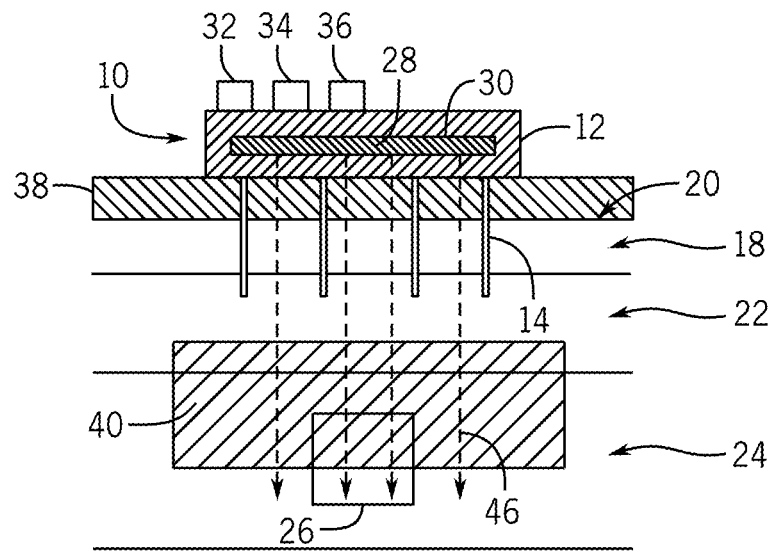
FIG. 1C illustrates a delivery system and a third stage of a method of its use, according to one aspect of the present disclosure.

Referring to FIG. 1C, the arrangement illustrated in FIGS. 1A and 1B is illustrated after the ultrasound probe 12 has begun emitting a second acoustic energy field 46 that penetrates at least through the membrane 18, the first material layer 22, and partially into the second material layer 24. In response to the second acoustic energy field 46, the transport target 40 can be driven from the first material layer 22 to a deeper portion of the first material layer 22 or into the second material layer 24.

It should be appreciated that there exist intermediate states between the state of the arrangement in FIG. 1B and that illustrated in FIG. 1C, where the second acoustic energy field 46 can penetrate throughout the first material layer 22, but not into the second material layer 24, or can penetrate into the second material layer 24 to a depth different than that illustrated. In similar intermediate states, the transport target 40 can penetrate throughout the first material layer 22, but not into the second material layer 24, or can penetrate into the second material layer 24 to a depth different than that illustrated.

Figure 1D:
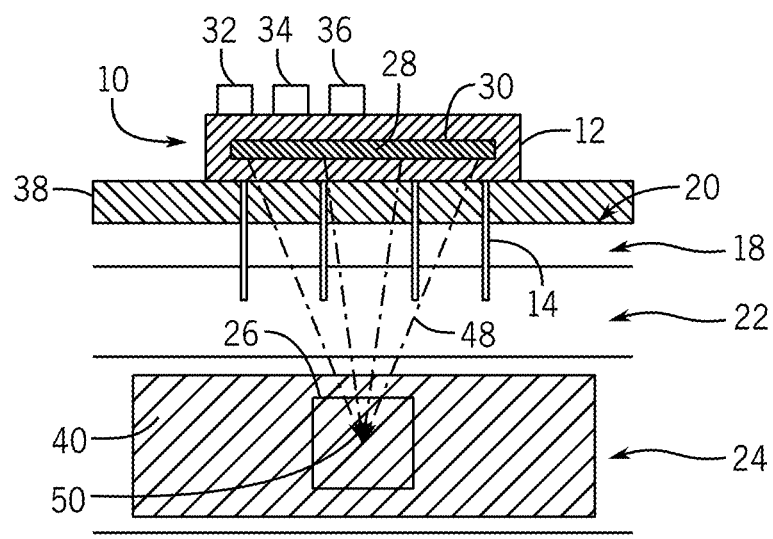
FIG. 1D illustrates a delivery system and a fourth stage of a method of its use, according to one aspect of the present disclosure.

Referring to FIG. 1D, the arrangement illustrated in FIGS. 1A, 1B, and 1C is illustrated after the transport target 40 has been driven into the second material layer 24. In the second material layer 24, the transport target 40 can interact with constituents within the second material layer 24. In certain aspects, a third acoustic energy field 48, optionally referred to as a therapeutic energy field 48, can be directed to a target volume 50 within the second material layer 24. In certain aspects, the third acoustic energy field 48 is substituted for a therapeutic energy field 48 that can include a photon-based therapeutic energy field, which can be generated by a photon-based source as described elsewhere herein, or a radiofrequency ("RF") therapeutic energy field, which can be generated by an RF electrode. The target volume 50 can be located in the first material layer 46 or a subsequent material layer. The target volume 50 can be located in a portion of the second material layer 24 containing the transport target 40.

The transport target 40 can be applied to the surface after the formation of the microchannels 42. The microneedles 14 and the ultrasound probe 12 can be part of the same instrument or can be separate. In aspects where they are separate, a device containing the microneedles 14 can be used to form the microchannels 42, the transport target 40 can be applied to the top membrane surface 20 prior to or subsequent to the formation of the microchannels 42, and the ultrasound probe can be coupled to the transport target 40, the top membrane surface 20, and the microchannels 42.

As will be described with respect to FIGS. 2A, 2B, 2C, and 2D, a delivery system 10 can include an ultrasound probe 12, a standoff 52 including a transport target 40, and one or more hollow microneedles 14 extending from a bottom standoff surface 54. The delivery system 10 can include features described elsewhere herein. The standoff 52 can include a plurality of pores in the bottom standoff surface 54, the plurality of pores each in fluid communication with the interior of a hollow microneedle 14. The plurality of pores and the interiors of the hollow microneedles 14 can be in fluid communication with the transport target 40. The plurality of pores can be of a size and shape that are sufficient to retain the transport target 40 within the standoff 52 when acoustic energy is not being applied. In certain aspects, the transport target 40 is retained in the standoff by virtue of a surface tension of the transport target 40. In certain aspects, the standoff is a gel pack coupled to the ultrasound source 12. In certain aspects, the standoff 52 can be rigid or flexible.

Figure 2A:
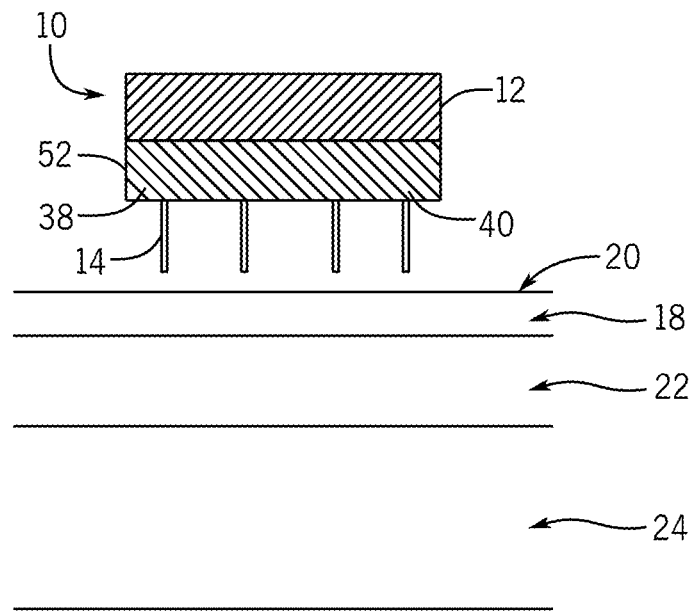
FIG. 2A illustrates a delivery system and a first stage of a method of its use, according to one aspect of the present disclosure.
Figure 2B:
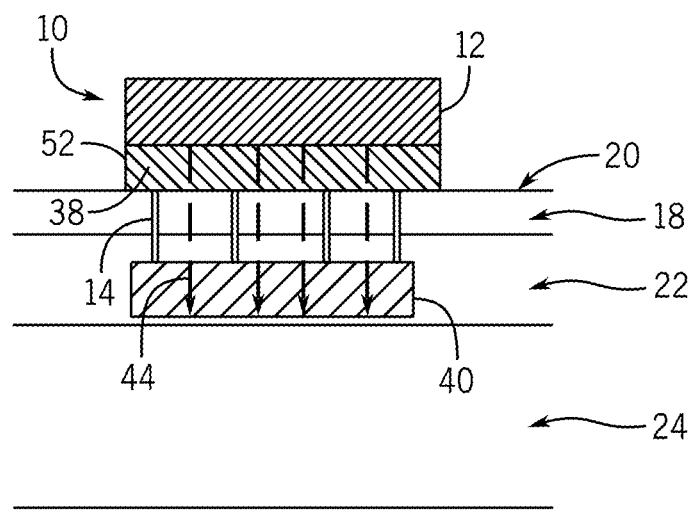
FIG. 2B illustrates a delivery system and a second stage of a method of its use, according to one aspect of the present disclosure.

Referring to FIG. 2A, the delivery system 10 is positioned above the top membrane surface 20. Referring to FIG. 2B, the arrangement illustrated in FIG. 2A is illustrated after the delivery system 10 has been coupled to the top membrane surface 20 and the hollow microneedles 14 have punctured the membrane 18, thereby traversing the membrane 18, and the ultrasound probe 12 has begun emitting a first acoustic energy field 44. The hollow microneedles 14 also produce microchannels 42 that extend over the full depth of the membrane 18. The first acoustic energy field 44 can penetrate at least through the membrane 18 and at least partially into the first material layer 22. In response to the first acoustic energy field 44, the transport target 40 can be driven from the standoff 52 into the first material layer 22.

It should be appreciated that there exist intermediate states between the state of the arrangement in FIG. 2A and that illustrated in FIG. 2B, where the delivery system 10 is positioned between the illustrated positions. There also exist intermediate states where the first acoustic energy field 44 penetrates only partially into the membrane 18, or penetrates throughout the membrane 18, but not into the first material layer 22, or penetrates throughout the membrane 18 and partially into the first material layer 22 to a depth different than that illustrated. In similar intermediate states, the transport target 40 can penetrate only partially into the hollow microneedles 14, or penetrates throughout the hollow microneedles 14, but not into the first material layer 22, or penetrates throughout the hollow microneedles 14 and partially into the first material layer 22 to a depth different than that illustrated.

Figure 2C:
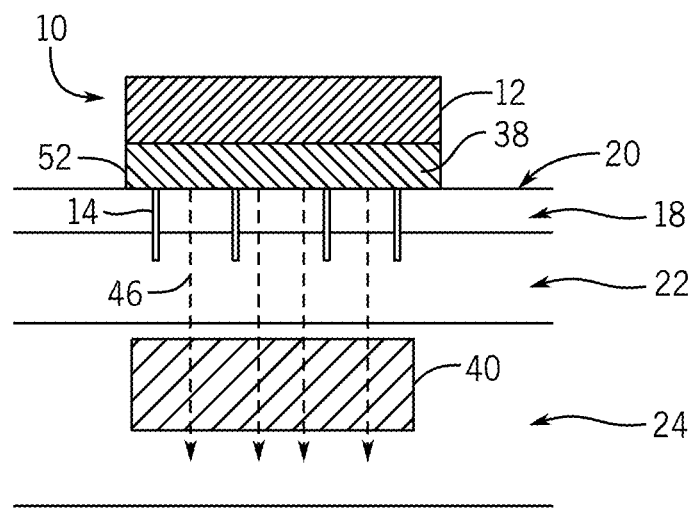
FIG. 2C illustrates a delivery system and a third stage of a method of its use, according to one aspect of the present disclosure.

Referring to FIG. 2C, the arrangement illustrated in FIGS. 2A and 2B is illustrated after the ultrasound probe 12 has begun emitting a second acoustic energy field 46 that penetrates at least through the membrane 18, the first material layer 22, and partially into the second material layer 24. In response to the second acoustic energy field 46, the transport target 40 can be driven from the first material layer 22 to a deeper portion of the first material layer 22 or into the second material layer 24.

It should be appreciated that there exist intermediate states between the state of the arrangement in FIG. 2B and that illustrated in FIG. 2C, where the second acoustic energy field 46 can penetrate throughout the first material layer 22, but not into the second material layer 24, or can penetrate into the second material layer 24 to a depth different than that illustrated. In similar intermediate states, the transport target 40 can penetrate throughout the first material layer 22, but not into the second material layer 24, or can penetrate into the second material layer 24 to a depth different than that illustrated.

Figure 2D:
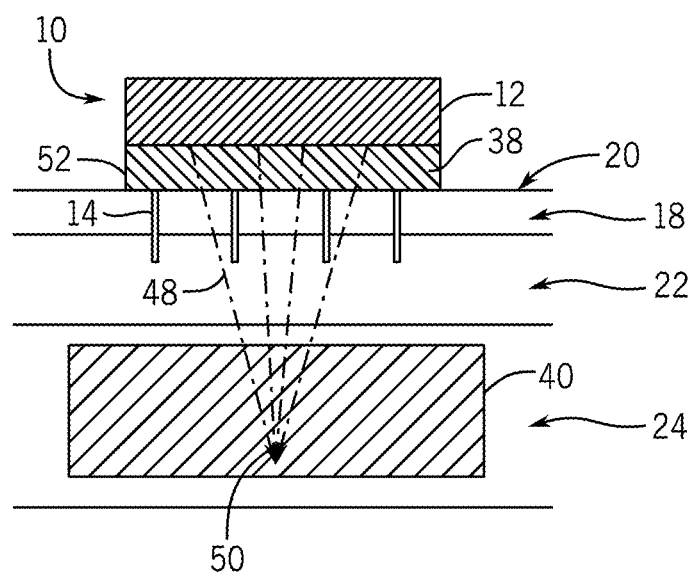
FIG. 2D illustrates a delivery system and a fourth stage of a method of its use, according to one aspect of the present disclosure.

Referring to FIG. 2D, the arrangement illustrated in FIGS. 2A, 2B, and 2C is illustrated after the transport target 40 has been driven into the second material layer 24. In the second material layer 24, the transport target 40 can interact with constituents within the second material layer 24. In certain aspects, a third acoustic energy field 48, optionally referred to as a therapeutic acoustic energy field 48, can be directed to a target volume 50 within the second material layer 24. The target volume 50 can be located in a portion of the second material layer 24 containing the transport target 40.

The first acoustic energy field 44, the second acoustic energy field 46, or the third acoustic energy field 48 can be planar, focused, weakly focused, unfocused, or defocused. The first acoustic energy field 44, the second acoustic energy field 46, or the third acoustic energy field 48 can have a frequency in the range of about 10 kHz to about 30 MHz, including, but not limited to, a frequency in the range of about 10 kHz to about 5 MHz, about 10 kHz to about 1 MHz, about 20 kHz to about 500 kHz, about 20 kHz to about 100 kHz, about 20 kHz to about 40 kHz, about 5 MHz to about 15 MHz, from about 2 MHz to about 12 MHz, from about 3 MHz to about 7 MHz, from about 1 MHz to about 7 MHz, from about 2 MHz to about 5 MHz, from about 3 MHz to about 10 MHz, or from about 1 MHz to about 10 MHz, or other combinations of the lower and upper limits of these ranges not explicitly recited. The first acoustic energy field 44, the second acoustic energy field 46, or the third acoustic energy field 48 can be configured to avoid damaging the material in the membrane 18 or in the first material layer 22.

The first acoustic energy field 44, the second acoustic energy field 46, or the third acoustic energy field 48 can be pulsed or continuous wave. In the case of pulsed acoustic energy, the first acoustic energy field 44, the second acoustic energy field 46, or the third acoustic energy field 48 can have a pulse width ranging from 33 ns to 100 seconds, including but not limited to, a pulse width ranging from 1 µs to 100 s, from 10 ms to 1 s, from 25 ms to 100 seconds, 1 ms to 5 s, from 1 µs to 1 s, or from 10 µs to 1 s.

In the case of pulsed acoustic energy, the first acoustic energy field 44, the second acoustic energy field 46, or the third acoustic energy field 48, the pulses can be separated by a length of time ranging from 1 µs to 1 s, including but not limited to, a length of time ranging from 10 µs to 1 s.

The first acoustic energy field 44, the second acoustic energy field 46, or the third acoustic energy field 48 can have a peak intensity ranging from 0.1 W/cm$^2$ to 70 kW/cm$^2$, including, but not limited to, a peak intensity ranging from 0.1 W/cm$^2$ to less than 5 W/cm$^2$, from 5 W/cm$^2$ to 70 kW/cm$^2$, from 10 W/cm$^2$ to 70 kW/cm$^2$, from 3 W/cm$^2$ to 20 kW/cm$^2$, from 3 W/cm$^2$ to 50 kW/cm$^2$, or other combinations of the lower and upper limits of these ranges not explicitly recited. The first acoustic energy field 44, the second acoustic energy field 46, or the third acoustic energy field 48 can have an average intensity ranging from 0.1 W/cm$^2$ to 1 kW/cm$^2$, including but not limited to, an average intensity ranging from 0.1 W/cm$^2$ to 10 W/cm$^2$, or from 5 W/cm$^2$ to 1 kW/cm$^2$.

In certain applications, the acoustic energy produced by the systems and utilized by the methods described herein can be a high-frequency and high-intensity acoustic energy. For these applications, the first acoustic energy field 44, the second acoustic energy field 46, or the third acoustic energy field 48 can have a frequency in the ranges disclosed above that are at least 1 MHz and a peak intensity in the ranges disclosed above that are at least 5 W/cm$^2$.

In certain applications, the acoustic energy produced by the systems and utilized by the methods described herein can be a low-frequency and low-intensity acoustic energy. For these applications, the first acoustic energy field 44, the second acoustic energy field 46, or the third acoustic energy field 48 can have a frequency in the ranges disclosed above that are less than 1 MHz and a peak intensity in the ranges disclosed above that are less than 5 W/cm$^2$.

Acoustic energy utilized for the generation of inertial cavitation or acoustic streaming can have a pulse width ranging from nanoseconds to seconds. In an example of a set of parameters suitable for generating an inertial cavitation effect or acoustic streaming effect, the first acoustic energy field 44, the second acoustic energy field 46, or the third acoustic energy field 48 can have a frequency ranging from 1 MHz to 30 MHz, and a peak intensity ranging from 5 W/cm$^2$ to 70 kW/cm$^2$. As an example of a set of parameters suitable for generating an inertial cavitation effect or acoustic streaming, the first acoustic energy field 44, the second acoustic energy field 46, or the third acoustic energy field 48 can have a frequency ranging from 2 MHz to 10 MHz, an average intensity ranging from 5 W/cm$^2$ to 1 kW/cm$^2$, delivering a pressure ranging from 10 kPa to 10 MPa. As an example of a set of parameters suitable for generating an inertial cavitation effect, the first acoustic energy field 44, the second acoustic energy field 46, or the third acoustic energy field 48 can have a frequency ranging from 10 kHz to less than 1 MHz, and a peak intensity ranging from 0.1 W/cm$^2$ to less than 5 W/cm$^2$.

In certain applications, such as generating inertial cavitation in the microchannels 42 or microneedles 14, the first acoustic energy field 44 can have a pulse width in a range from about 33 ns to about 100 s. In these certain applications, the first acoustic energy field 44 can be pulsed and can have a pulse width in the range of about 1 µs to about 1 second, or in the range of about 0.01 seconds to about 5 seconds. In these certain applications, the first acoustic energy field 44 can have a peak intensity of greater than 3 W/cm$^2$ and less than or equal to about 100 kW/cm$^2$ at the top membrane surface 20. The intensity of the first acoustic energy field 44 can be below a threshold value for creating a shock wave. A person having ordinary skill in the art will appreciate that this threshold value can vary based on material properties and the specific parameters of the ultrasound being used, and can determine this threshold value for specific materials and sets of parameters experimentally or computationally.

In certain applications, such as generating acoustic streaming providing acoustic streaming pressure to the microchannels 42, the microneedles 14, the first material layer 22, or a combination thereof, the first acoustic energy field 44 can be pulsed and the pulses can have a pulse width in a range of about 1 µs to about 100 s, including, but not limited to, a range of about 0.001 seconds to about 5 seconds. In these certain applications, the first acoustic energy field 44 can have a peak intensity in the range from about 5 W/cm$^2$ to about 100 kW/cm$^2$ at the top membrane surface 20. Acoustic streaming can generate micro-channels having a transcellular route from the top membrane surface 20 to the first material layer 22. In these certain applications, acoustic streaming generated by the first acoustic energy field 44 can create pressures ranging from about 10 kPa to about 120 MPa, including, but not limited to, pressures ranging from about 10 kPa to about 10 MPa and pressures ranging from about 10 MPa to about 120 MPa, in the microchannels 42, the microneedles 14, the first material layer 22, or a combination thereof.

In certain applications, such as generating inertial cavitation and acoustic streaming to the microchannels 42, the microneedles 14, the first material layer 22, or a combination thereof, the first acoustic energy 44 can provide two or more effects, such as inertial cavitation and acoustic streaming, simultaneously or alternating. In certain aspects, generating inertial cavitation and acoustic streaming can facilitate moving a larger medicant, such as a medicant with a molecular weight greater than 500 Da, through the membrane 18.

In certain applications, the second acoustic energy 46 can be configured to generate inertial cavitation or acoustic streaming in the first material layer 22, the second material layer 24, or a combination thereof. In certain aspects, the second acoustic energy 46 can be configured to increase diffusion of the transport target 40 through the first material layer 22 and the second material layer 24. In certain aspects, the second acoustic energy 46 can provide a pressure in a range from about 100 kPa to about 100 MPa to push the transport target 40 through the first material layer 22 and into the second material layer 24.

It should be appreciated that the effects described herein are material-dependent, so the ultrasound energy necessary to generate inertial cavitation or acoustic streaming in one type of material might be different than the ultrasound energy necessary to generate inertial cavitation or acoustic streaming in a different type of material. It should also be appreciated that for a certain effect to be generated, the threshold for generating that effect must be exceeded. However, the thresholds for generating the effects described herein, such as inertial cavitation and subsequent acoustic streaming, in certain materials, such as tissues, are generally unknown.

With respect to inertial cavitation in tissue, aside from a single experimental study regarding the frequency-dependence of the threshold for inertial cavitation in canine skeletal muscle, a recent article by Church et al. states that "too little information on the experimental threshold for inertial cavitation in other tissues is available" to make conclusions regarding frequency-dependent trends. See, Church C C, et al. "Inertial cavitation from ARFI imaging and the MI", Ultrasound in Med. & Biol., Vol. 41, No. 2, pp. 472-485 (2015). This observation is solely about the inertial cavitation threshold as it relates to frequency, and does not take into account the other spatial and temporal parameters aside from frequency. Accordingly, one of skill in the art should appreciate that the present invention is disclosed in terms of effects that have been shown to produce a specific result, i.e., transporting a medicant across the stratum corneum, and a set of general parameters that are suitable for achieving that result are set forth above. One of skill in the art should also appreciate that the presence of inertial cavitation can be identified by a characteristic broadband signal that is the result of the complex dynamics associated with inertial cavitation.

With respect to acoustic streaming, this effect can be generated by an effect including the aforementioned inertial cavitation or without the inertial cavitation. In instances without the inertial cavitation, acoustic streaming can be accomplished by introducing heat into a tissue, for example the stratum corneum, which expands the tissue, then applying a pressure to the medicant or a carrier containing the medicant to initiate acoustic streaming.

The inertial cavitation and acoustic streaming effects are described herein with respect to the discrete layers of the skin, but can penetrate to a greater depth beneath the skin surface to enhance the penetration of the medicant deeper into the skin or into subcutaneous tissue.

In certain aspects, the first acoustic energy 44 and the second acoustic energy 46 can be substantially the same. In certain aspects, the second acoustic energy 46 can have a frequency that concentrates the acoustic energy deeper and moves the transport target 40 into the second material layer 24.

In certain aspects, the second acoustic energy 46 or third acoustic energy 48 can be configured to cause a thermal effect in the first material layer 22 or the second material layer 24, which is non-destructive to the first material layer 22 or second material layer 24. The thermal effect can elevate the temperature of the first material layer 22 or the second material layer 24, which can enhance dispersion of the transport target 40 within the first material layer 22 or the second material layer 24.

The first acoustic energy 44, second acoustic energy 46, or third acoustic energy 48 can be generated from one or more ultrasound sources.

In certain aspects, the delivery system 10 can be configured to create an intensity gain from the delivery system 10 to the target volume 50 of at least about 5, including, but not limited to, an intensity gain of at least about 10, at least about 25, at least about 50, at least about 100, or at least about 500. In aspects having a focused or a strongly focused ultrasound, the delivery system 10 can be configured to create an intensity gain from the delivery system 10 to the target volume 50 of at least about 50, including, but not limited to, an intensity gain of at least about 100, or at least about 500, or a gain ranging from 500 to 50,000. In aspects having a weakly focused ultrasound, the delivery system 10 can be configured to create an intensity gain from the delivery system 10 to the target volume 50 of at least about 5 or a gain ranging from 5 to 500.

In certain aspects with pulsed ultrasound, a first pulse can be ultrasound having a first type of focus, a second pulse can be ultrasound having a second type of focus, a third pulse can be ultrasound having the first type of focus or a third type of focus, and so on. Any of a variety of combinations of focused, defocused, or unfocused energy can be used for any of the various pulses.

In certain aspects, the first acoustic energy 44, second acoustic energy 46, or third acoustic energy 48 can create a thermal effect, a mechanical effect, or a combination thereof in the target volume 50. A mechanical effect is a non-thermal effect within a medium that is created by acoustic energy. A mechanical effect can be one of, for example, acoustic resonance, acoustic streaming, disruptive acoustic pressure, shock waves, inertial cavitation, and non-inertial cavitation.

The thermal effect can elevate the temperature by about 1° C. to about 65° C., including but not limited to, elevating the temperature by about 1° C. to about 15° C. or by about 15° C. to about 65° C.

Figure 3A:
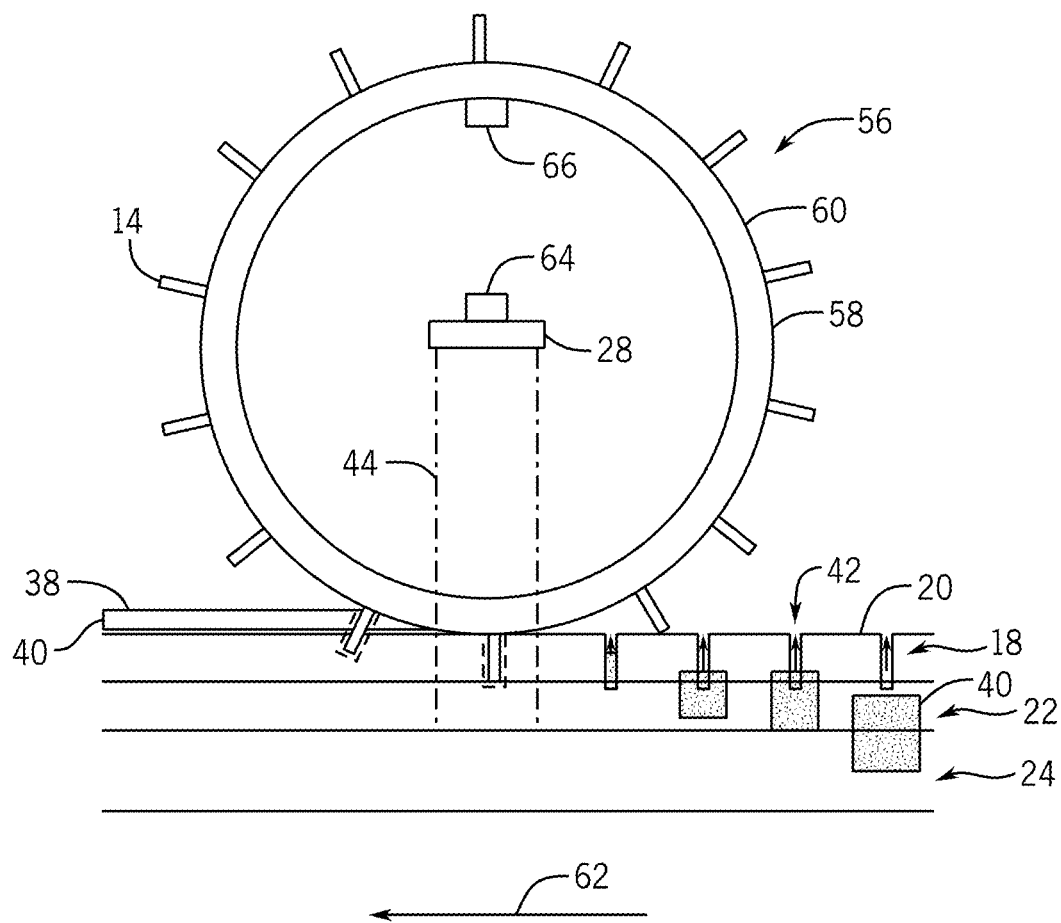
FIG. 3A illustrates a roller delivery system and methods of its use, according to one aspect of the present disclosure.

Referring to FIG. 3A, a variation on the delivery system 10 is a roller delivery system 56. The roller delivery system 56 can take a variety of shapes that are suitable for rolling along a surface, but is illustrated as a cylinder 58 comprising a plurality of microneedles 14 projecting from an outer cylinder surface 60. The roller delivery system 56 can be coupled to a top membrane surface 20 and can be moved along a direction 62 by a user or another means of impulsion, including but not limited to, robotic means of impulsion, automatic means of impulsion, and the like. A layer of coupling medium 38 including a transport target 40 can be positioned atop the top membrane surface 20. When moving along the top membrane surface 20, the microneedles 14 can puncture the membrane 18, thereby producing microchannels 42 in the membrane. The microchannels 42 can extend over the full depth of the membrane 18.

In one aspect, the roller delivery system 56 can be configured to direct a first acoustic energy field 44 into an area including a microchannel 42, thereby driving the transport target 40 into or through the microchannel 42. The transport target 40 can be directed into the first material layer 22 by the first acoustic energy field 44. The transport target 40 can then diffuse deeper into the first material layer 22 or into the second material layer 24, or can be driven deeper into the first material layer 22 or into the second material layer 24 by a subsequent acoustic energy field (not pictured). In some aspects, the ultrasound 28 can include multiple transducers 30 or transduction elements that are fired in a time fashion to continue directing the first acoustic energy field 44 into the microchannel 42 even as the roller delivery system 56 moves along the direction 62 and away from the microchannel 42.

The roller delivery system 56 can include a position sensor 64 for sensing the position of the roller delivery system 56 as it moves in the direction 62. The roller delivery system 56 can include an orientation sensor 66 for sensing the relative orientation of the microneedles 14 in relation to the ultrasound source 28. The roller delivery system 56 can include one or more of the features described elsewhere for the delivery system 10.

Figure 3B:
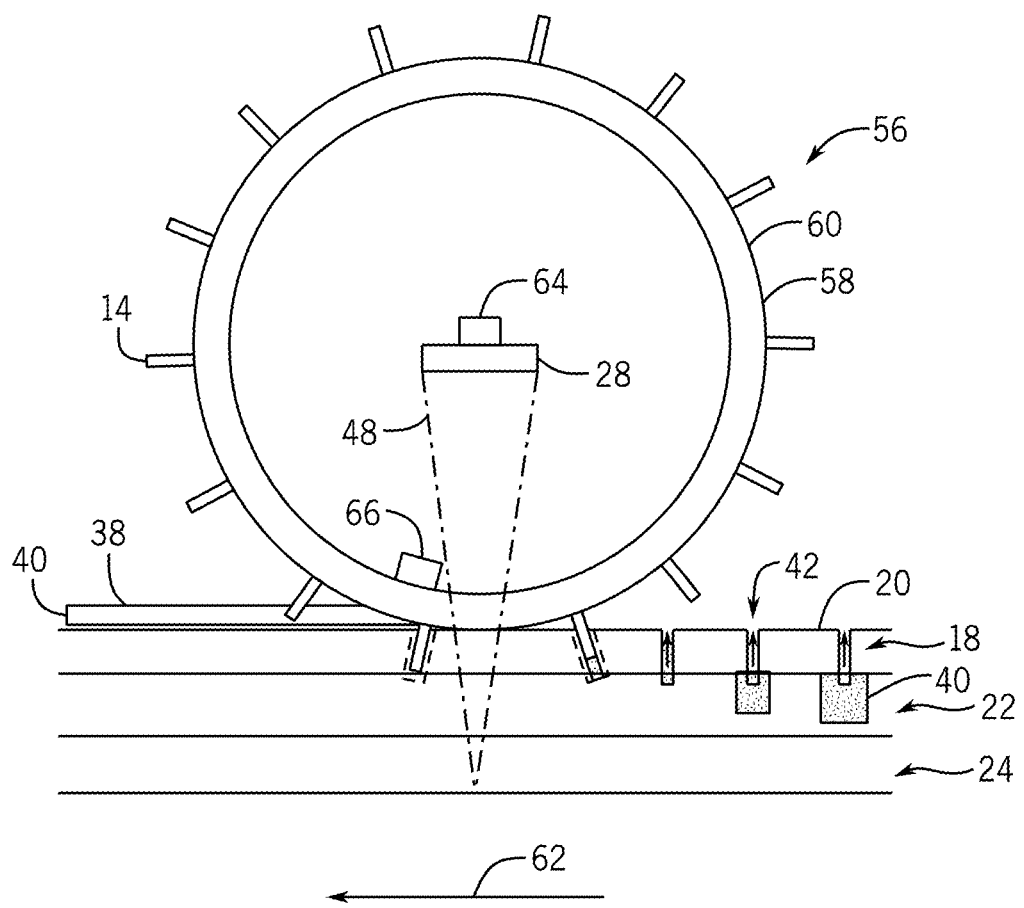
FIG. 3B illustrates a roller delivery system and methods of its use, according to one aspect of the present disclosure.

Referring to FIG. 3B, the roller delivery system 56 can be configured to direct a therapeutic energy field 48, such as an acoustic energy field, into a target volume 50. The target volume 50 can be located beneath a microchannel 42. To achieve this, the control module 36 can be programmed with the distance between microneedles 14, which is the distance between the microchannels 42 that they create in the membrane. The control module 36 can then direct the ultrasound source 28 to direct the therapeutic energy field 48 to the target volume 50 in a pulsed manner after the roller delivery system 56 has moved the distance between the microchannels 42. Alternatively, or in combination, the control module 36 can be programmed to receive from the orientation sensor 66 the relative orientation of the microneedles 14 relative to the ultrasound source 28, and can be programmed to direct the ultrasound source 28 to direct the therapeutic energy field 48 to the target volume 50 in a pulsed manner when the orientation sensor 66 indicates that a microneedle is located beneath the ultrasound source 28.

Figure 4:
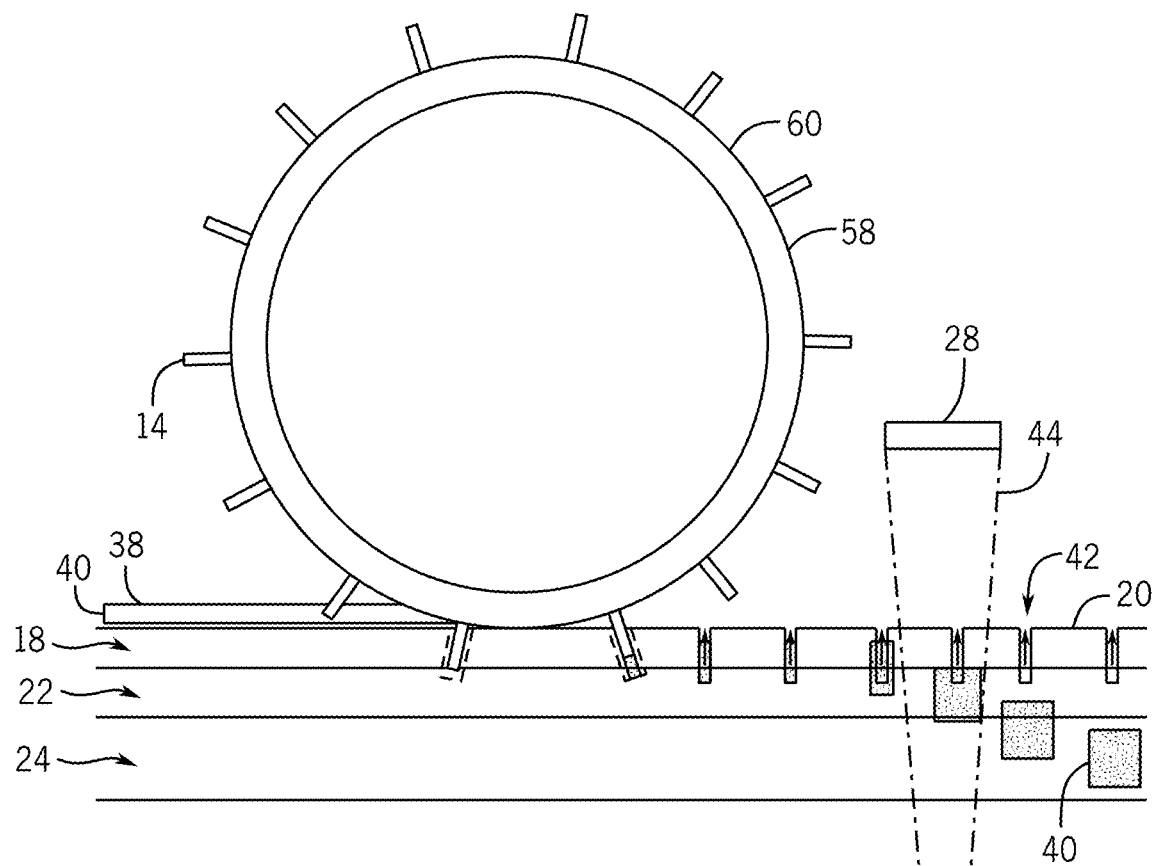
FIG. 4 illustrates a roller delivery system and methods of its use, according to one aspect of the present disclosure.

Referring to FIG. 4, the roller delivery system 56 can include an ultrasound source 28 that is not contained within the cylinder 58. In this aspect, the ultrasound source 28 can direct a first acoustic energy field 44, a second acoustic energy field 46, or other acoustic energy field described herein into the microchannel 42, the membrane 18, the first material layer 22, the second material layer 24, or a combination thereof.

In some aspects, the cylinder 58 and the ultrasound source 28 are contained within the same device. In some aspects, the cylinder 58 and the ultrasound source 28 are contained in different devices.

The roller delivery system 56 can further include one or more of the aspects disclosed in U.S. patent application Ser. No. 14/569,001, filed Dec. 12, 2014, which is incorporated herein in its entirety by reference.

As will be discussed with respect to FIGS. 5A, 5B, 5C, and 5D, a delivery system 10 can be in the form of a photon-emitting delivery system 68. The photon-emitting delivery system 68 can include a photon probe 70 including a photon source 72 and features of the delivery system 10 described elsewhere herein, in particular, features described with respect to FIGS. 2A, 2B, 2C, and 2D. In some aspects, the photon-emitting delivery system 68 can include can include the photon probe 70, the photon source 72, a standoff 52 including a transport target 40, and one or more hollow microneedles 14 extending from the bottom standoff surface 54.

Figure 5A:
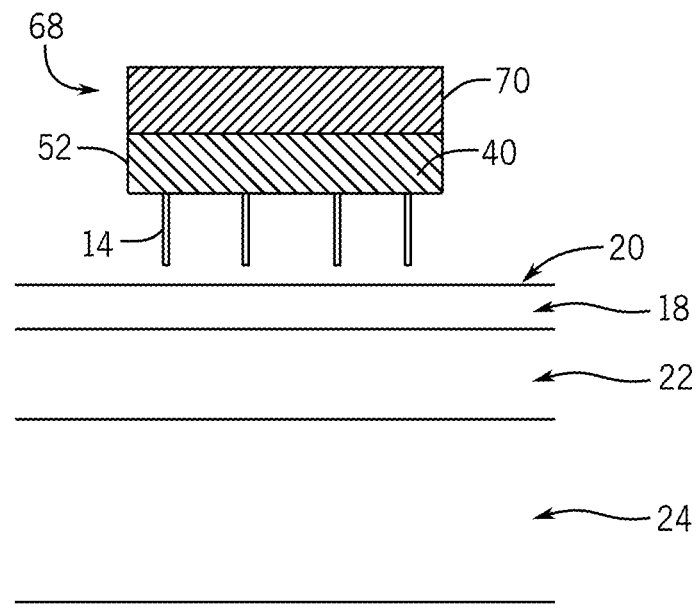
FIG. 5A illustrates a photon-emitting delivery system and a first stage of a method of its use, according to one aspect of the present disclosure.
Figure 5B:
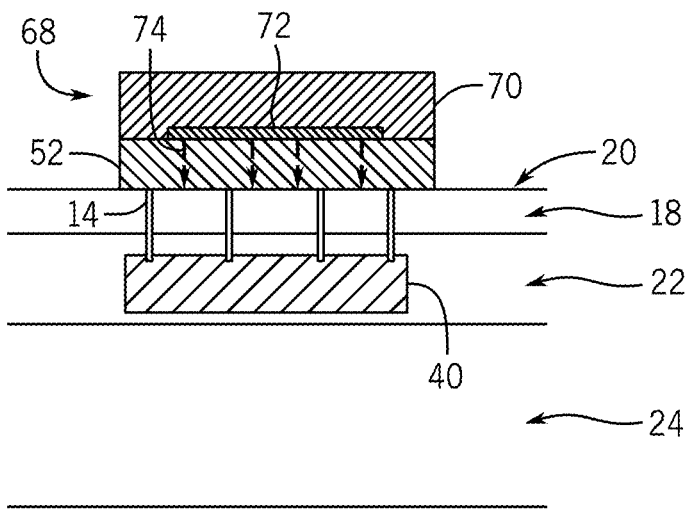
FIG. 5B illustrates a photon-emitting delivery system and a second stage of a method of its use, according to one aspect of the present disclosure.

Referring to FIG. 5A, the photon-emitting delivery system 68 is positioned above the top membrane surface 20. Referring to FIG. 5B, the arrangement illustrated in FIG. 5A is illustrated after the photon-emitting delivery system 68 has been coupled to the top membrane surface 20 and the hollow microneedles 14 have punctured the membrane 18, thereby creating microchannels 42 in the membrane 18, and the photon probe 70 has begun emitting a first photon-based energy field 74. The first photon-based energy field 74 can be directed into the standoff 52 and is configured to move the transport target 40 through the hollow microneedles 14 and into the first material layer 22. In some aspect, the first photon-based energy field 74 can be configured to initiate a photoacoustic effect within the standoff to generate pressure that causes the transport target 40 to move through the hollow microneedles 14 and into the first material layer 22. Without wishing to be bound by any particular theory, it is believed that the photoacoustic effect can create a rapid thermalization via absorption of the first photon-based energy field 74, which can initiate an expansion of the transport target 40 in the location where the first photon-based energy field 74 is delivered, thereby producing an acoustic wave.

In certain aspects, the standoff 52 can be configured as an acoustic amplifier, which can amplify the Q factor of the photoacoustic energy generated by the first photon-based energy field 74 from 10 times to 1000 times.

In certain aspects, the photon-emitting delivery system 68 can be configured in the same fashion as the delivery system 10 described with respect to FIGS. 1A, 1B, 1C, and 1D, and the first photon-based energy field can be configured to drive the transport target 40 through the microchannels 42 and into the first material layer 22.

Figure 5C:
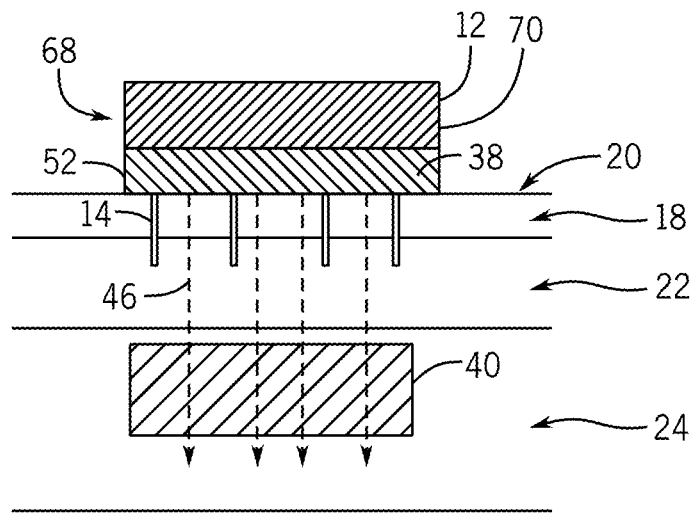
FIG. 5C illustrates a photon-emitting delivery system and a third stage of a method of its use, according to one aspect of the present disclosure.

Referring to FIG. 5C, the photon-emitting delivery system 68 can optionally include the ultrasound probe 12 and can function in the fashion described above for FIG. 2C with respect to the delivery system 10.

Figure 5D:
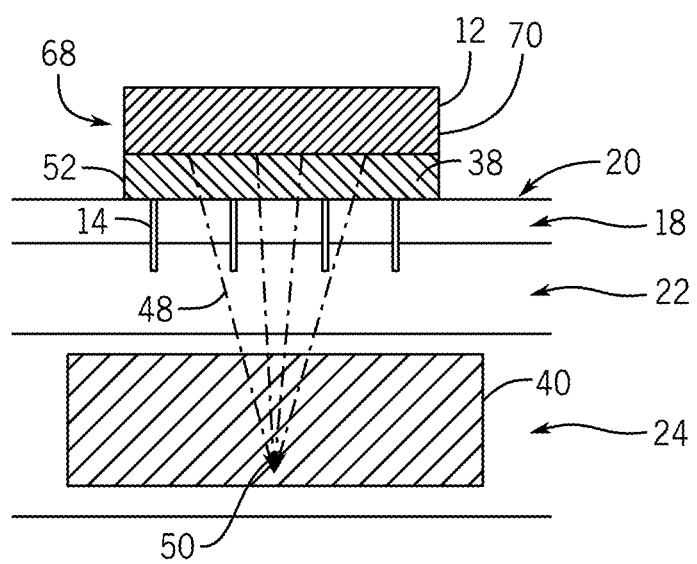
FIG. 5D illustrates a photon-emitting delivery system and a fourth stage of a method of its use, according to one aspect of the present disclosure.

Referring to FIG. 5D, the photon-emitting delivery system can optionally deliver a therapeutic energy field 48 to a target volume 50 in the second material layer 24 as described elsewhere herein. The therapeutic energy field 48 that can include an acoustic therapeutic energy field, which can be generated by the ultrasound source 28, a photon-based therapeutic energy field, which can be generated by a photon source 72, or an RF therapeutic energy field, which can be generated by an RF electrode.

It should be appreciated that there exist intermediate states between the state of the arrangement in FIG. 5A and that illustrated in FIG. 5B, between the state of the arrangement in FIG. 5B and that illustrated in FIG. 5C, and between the state of the arrangement in FIG. 5C and that illustrated in FIG. 5D, as described elsewhere herein.

As will be described with respect to FIGS. 6A, 6B, 6C, 6D, and 6E, a delivery system 10 can be in the form of a remote microchannel generating delivery system 76. The delivery system 76 can include an ultrasound probe 12 and a remote microchannel probe 78. The remote-microchannel probe 78 can include a photon source 72 configured to ablate the membrane 18 and optionally the first material layer 22 or second material layer 24 in a spatially-controlled fashion to generate microchannels 42 therein.

Figure 6A:
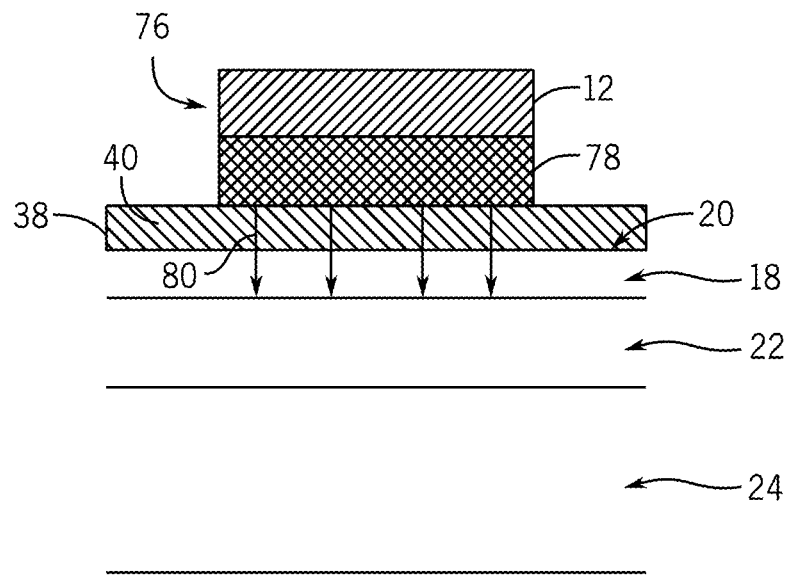
FIG. 6A illustrates a remote microchannel generating delivery system and a first stage of a method of its use, according to one aspect of the present disclosure.

Referring to FIG. 6A, the delivery system 76 is illustrated positioned above the top membrane surface 20. A layer of coupling medium 38 is positioned atop the top membrane surface 20. The coupling medium 38 can include a transport target 40. In some aspects, the transport target 40 can be dispersed or dissolved in the coupling medium 38. In some aspects, the coupling medium 38 itself can be the transport target 40. The remote microchannel probe 78 has begun emitting a second photon-based energy field 80 into the membrane 18 and partially into the first material layer 22.

Figure 6B:
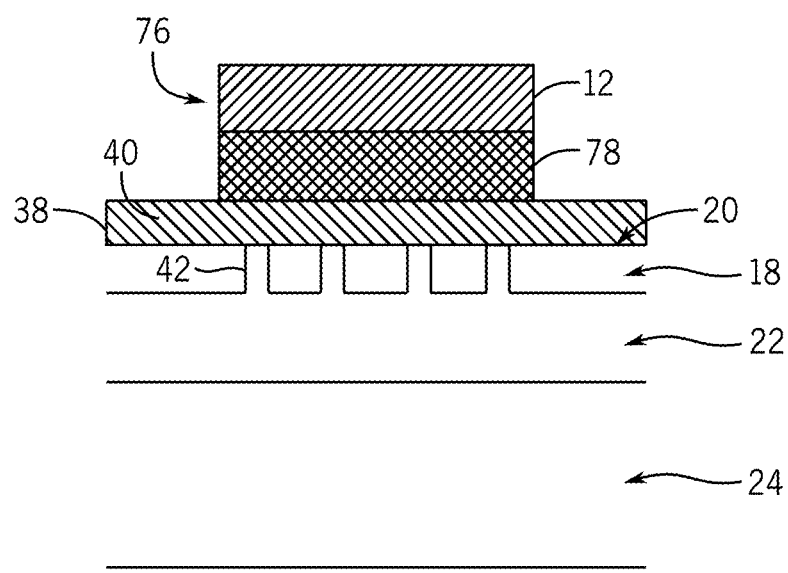
FIG. 6B illustrates a remote microchannel generating delivery system and a second stage of a method of its use, according to one aspect of the present disclosure.

Referring to FIG. 6B, the arrangement illustrated in FIG. 6A is illustrated after the remote microchannel probe 78 has generated microchannels 42 in the membrane 18.

Figure 6C:
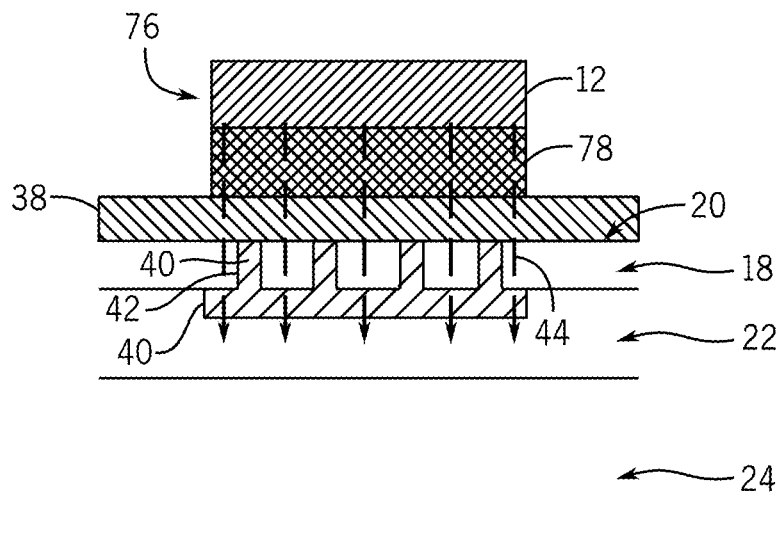
FIG. 6C illustrates a remote microchannel generating delivery system and a third stage of a method of its use, according to one aspect of the present disclosure.

Referring to FIG. 6C, the arrangement illustrated in FIG. 6B is illustrated after the ultrasound probe 12 has begun emitting a first ultrasound energy field 44. The microchannels 42 extend over the full depth of the membrane 18. The first acoustic energy field 44 can penetrate at least through the membrane 18 and at least partially into the first material layer 22. In response to the first acoustic energy field 44, the transport target 40 can be driven from above the top membrane surface 20, into or through the microchannels 42, and into the first material layer 22.

Figure 6D:
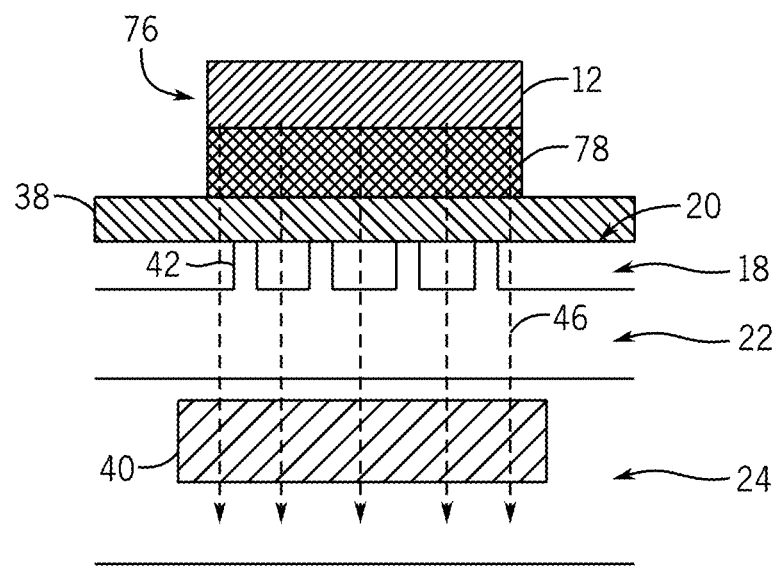
FIG. 6D illustrates a remote microchannel generating delivery system and a fourth stage of a method of its use, according to one aspect of the present disclosure.

Referring to FIG. 6D, the arrangement illustrated in FIG. 6C is illustrated after the ultrasound probe 12 has begun emitting a second acoustic energy field 46 that penetrates at least through the membrane 18, the first material layer 22, and partially into the second material layer 24. In response to the second acoustic energy field 46, the transport target 40 can be driven from the first material layer 22 to a deeper portion of the first material layer 22 or into the second material layer 24.

Figure 6E:
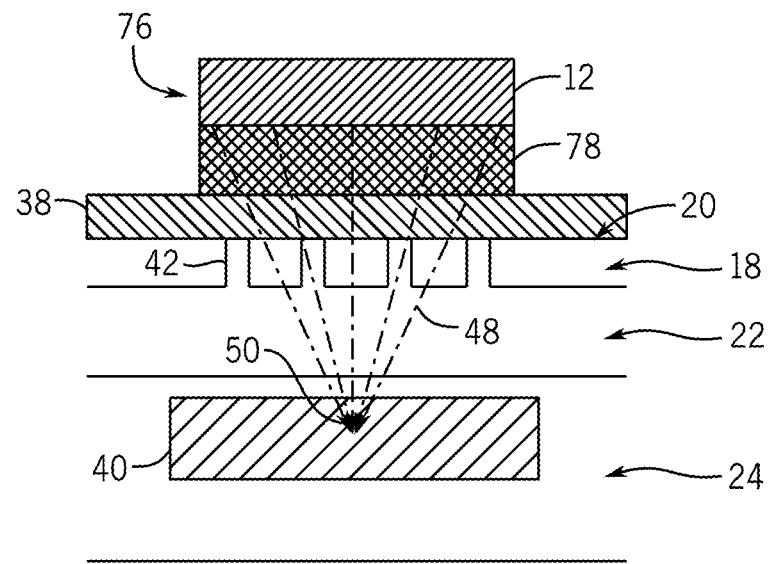
FIG. 6E illustrates a remote microchannel generating delivery system and a fifth stage of a method of its use, according to one aspect of the present disclosure.

Referring to FIG. 6E, the arrangement illustrated in FIG. 6D is illustrated after the transport target 40 has been driven into the second material layer and a therapeutic energy field 48 has been directed to a target volume 50 within the second material layer 24. The operation illustrated in FIG. 6E can function substantially the same as that described above with respect to FIG. 1D.

It should be appreciated that there exist intermediate states between the state of the arrangement in FIG. 6A and that illustrated in FIG. 6B, between the state of the arrangement in FIG. 6B and that illustrated in FIG. 6C, between the state of the arrangement in FIG. 6C and that illustrated in FIG. 6D, and between the state of the arrangement in FIG. 6D and that illustrated in FIG. 6E, as described elsewhere herein.

Figure 7:
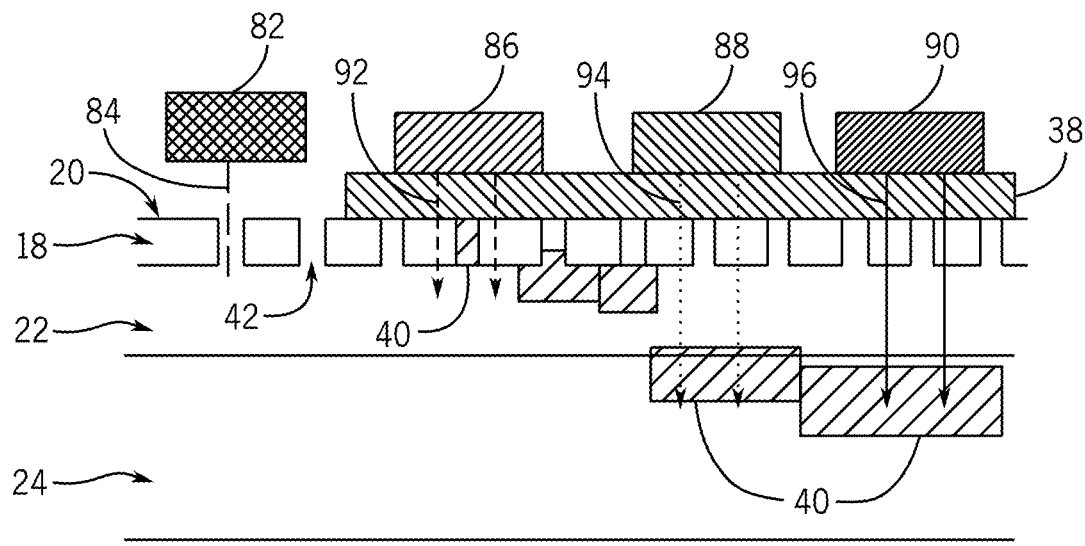
FIG. 7 illustrates a set of components for use in an ultrasound assisted drug delivery system, according to one aspect of the present disclosure.

Referring to FIG. 7, multiple devices, including a microchannel device 82 comprising a microchannel creation means 84, a first ultrasound device 86, a second ultrasound device 88, and a third ultrasound device 90, can be configured individually or as a part of a single system to independently or cooperatively provide delivery of a transport target 40. The microchannel device 82 comprising the microchannel creation means 84 is configured to create a microchannel 42 through the membrane 18. The microchannel creation means 84 can be one of a variety of the systems or methods described herein as being capable of producing a microchannel 42. For example, the microchannel creation means 84 can employ one or more acoustic energy fields, such as those described elsewhere herein. The microchannel creation means 84 can also include one or more microneedles. The microchannel creation means 84 can include a second photon-based energy field 80 configured to generate microchannels 42 in the membrane 18.

The microchannel device 82, the first ultrasound device 86, the second ultrasound device 88, and the third ultrasound device 90 can move from right to left across the illustrated top membrane surface 20, either collectively or independently. A coupling medium 38 can be applied to the top membrane surface 20 before or after the microchannel creation means 84 has created a microchannel 42. If the microchannel device 82, the first ultrasound device 86, the second ultrasound device 88, and the third ultrasound device 90 are operating in series, then the coupling medium 38 is typically applied to the top membrane surface 20 after the microchannel creation means 84 has created the microchannel 42 to avoid loss of the transport target 40 or contamination of the transport target 40 by the microchannel creation means 84. The microchannel device 82, the first ultrasound device 86, the second ultrasound device 88, and the third ultrasound device 90 can be controlled by a control module 36, either collectively or independently. In certain aspects, the microchannel device 82, the first ultrasound device 86, the second ultrasound device 88, and the third ultrasound device 90 can each be housed in individual cylinders or spheres that are configured to roll across the top membrane surface 20.

The first ultrasound device 86 can be configured to direct a fourth acoustic energy field 92 into the top membrane surface 20. The fourth acoustic energy field 92 can be configured to drive the transport target 40 through the microchannel 42. In certain aspect, the fourth acoustic energy field 92 can have the properties of the first acoustic energy field 44, as described herein.

The second ultrasound device 88 can be configured to direct a fifth acoustic energy field 94 into the top membrane surface 20. The fifth acoustic energy field 94 can be configured to drive the transport target 40 through the first material layer 22 and optionally through the second material layer 24. In certain aspects, the fifth acoustic energy field 94 can have the properties of the second acoustic energy field 46, as described herein.

The third ultrasound device 90 can be configured to direct a sixth acoustic energy field 96 into the top membrane surface 20. The sixth acoustic energy field 96 can be configured to interact with the transport target 40 or with tissue containing or proximate to the transport target 40. In certain aspect, the sixth ultrasound acoustic energy field 96 can have the properties of the third acoustic energy field 48, as described herein.

In addition to the first acoustic energy field 44, the second acoustic energy field 46, the third acoustic energy field 48, the fourth acoustic energy field 92, the fifth acoustic energy field 94, or the sixth acoustic energy field 96, the methods described herein can utilize additional acoustic energy fields configured to provide one or more effects described herein.

Figure 8A:
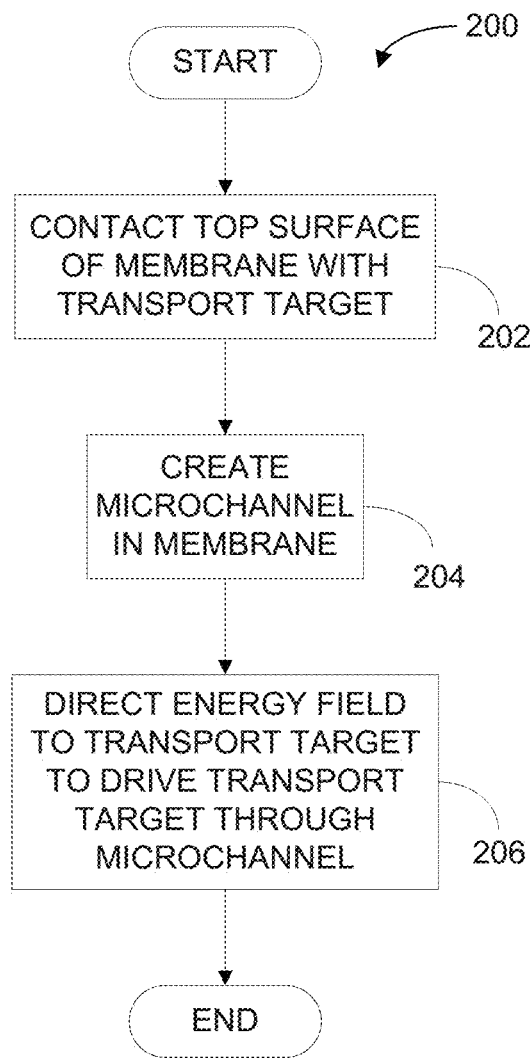
FIG. 8A is a flowchart illustrating a method of ultrasound assisted drug delivery, according to one aspect of the present disclosure.

Referring to FIG. 8A, this disclosure provides a method 200 for transporting a transport target across a membrane. At process block 202, the method 200 can include contacting a top surface of the membrane with the transport target. At process block 204, the method 200 can include creating a microchannel in the membrane. At process block 206, the method 200 can include directing an acoustic energy field or a photon-based energy field to the transport target, thereby driving the transport target through the microchannel.

Figure 8B:
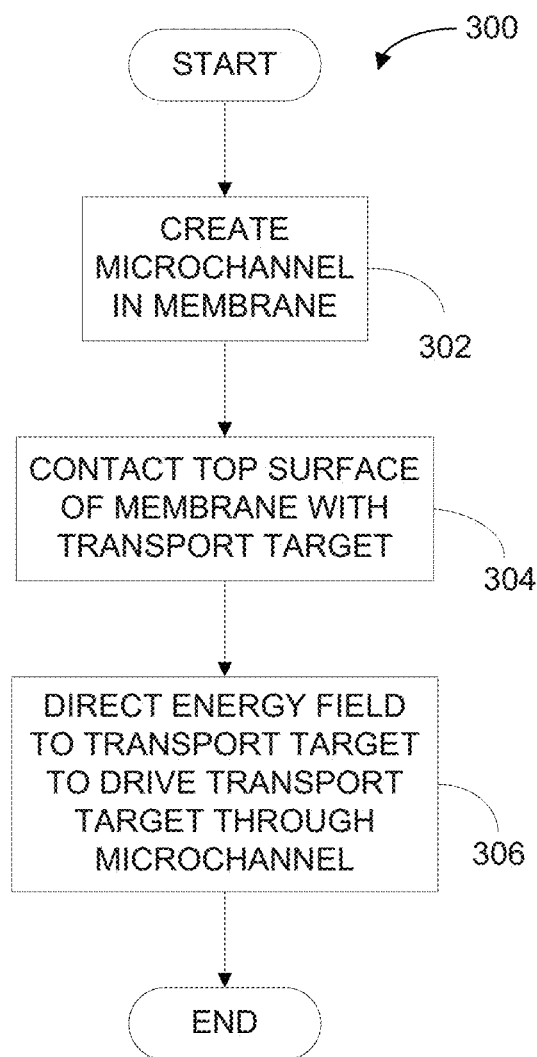
FIG. 8B is a flowchart illustrating a method of ultrasound assisted drug delivery, according to one aspect of the present disclosure.

Referring to FIG. 8B, this disclosure provides a method 300 for transporting a transport target across a membrane. At process block 302, the method 300 can include creating a microchannel in the membrane. At process block 304, the method 300 can include contacting a top surface of the membrane with the transport target. At process block 306, the method 300 can include directing an acoustic energy field or a photon-based energy field to the transport target, thereby driving the transport target through the microchannel.

Figure 8C:
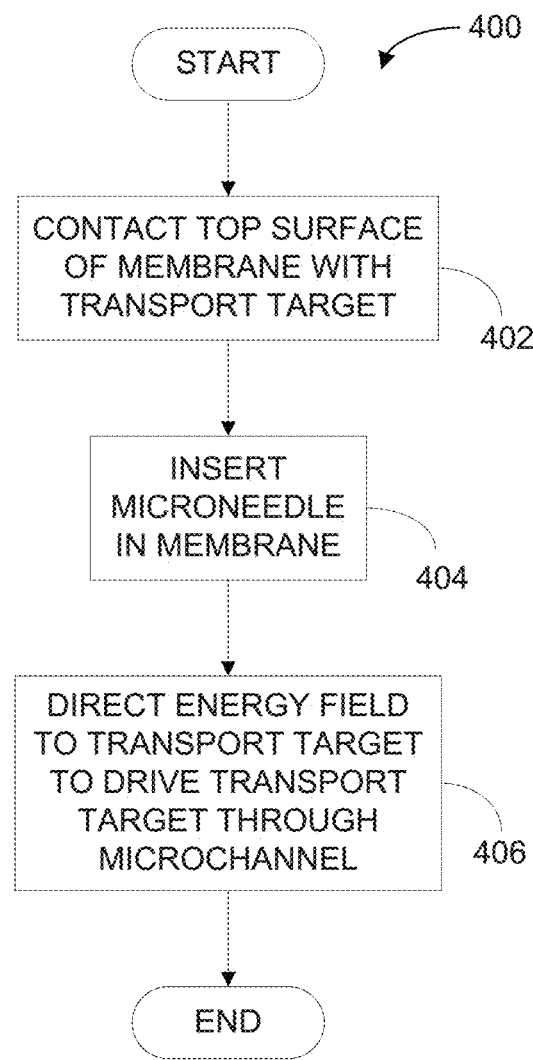
FIG. 8C is a flowchart illustrating a method of ultrasound assisted drug delivery, according to one aspect of the present disclosure.

Referring to FIG. 8C, this disclosure provides a method 400 for transporting a transport target across a membrane. At process block 402, the method 400 can include contacting a top surface of the membrane with the transport target. At process block 404, the method 400 can include inserting a hollow microneedle in the membrane. At process block 406, the method can include directing an acoustic energy field or a photon-based energy field to the transport target, thereby driving the transport target through the microneedle.

Figure 8D:
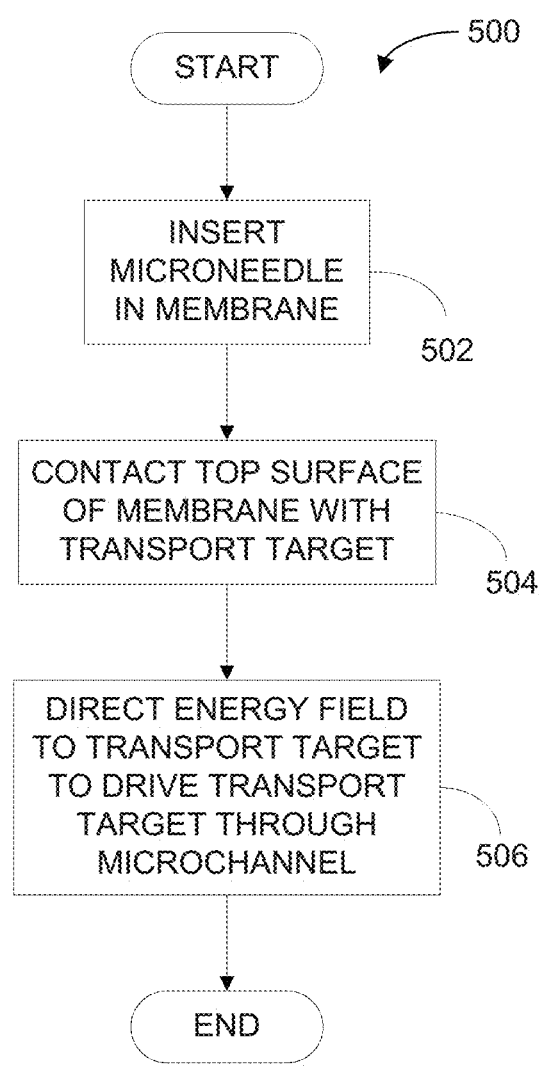
FIG. 8D is a flowchart illustrating a method of ultrasound assisted drug delivery, according to one aspect of the present disclosure.

Referring to FIG. 8D, this disclosure provides a method 500 for transporting a transport target across a membrane. At process block 502, the method 500 can include inserting a hollow microneedle in the membrane. At process block 504, the method 500 can include contacting a top surface of the membrane with the transport target. At process block 506, the method can include directing an acoustic energy field or a photon-based energy field to the transport target, thereby driving the transport target through the microneedle.

A person having ordinary skill in the art will appreciate that in some aspects, the properties of the transport target can help determine whether the transport target is applied to the surface prior to or subsequent to the generation of microchannels and/or the insertion of microneedles. For example, if the means of generating the microchannels involves In certain aspects, the membrane 18 can be a stratum corneum layer of skin, the top membrane surface 20 can be a surface of skin, the first material layer 22 can be an epidermis layer of skin, and the second material layer 24 can be a dermis layer of skin. When the transport target 40 has been delivered to the dermis layer of skin, the transport target 40 can interact with the tissue therein or enter the blood stream via capillaries.

The transport target 40 can be mixed into or can be a component of a carrier. The carrier can be biocompatible. Examples of a biocompatible carrier include, but are not limited to, glycerin, liposomes, nanoparticles, microbubbles, and the like. In certain aspects, the carrier can enhance and/or lower the threshold for inertial cavitation.

The transport target 40 can be a medicant.

In certain aspect, the methods described herein can achieve transport of greater than 1 µL per minute of the transport target 40 across the membrane 18, including, but not limited to, greater than 5 µL per minute, greater than 10 µL per minute, greater than 20 µL per minute, greater than 40 µL per minute, greater than 50 µL per minute, or greater than 75 µL per minute of transport target 40 across the membrane 18.

The medicant can be mixed into or be a component of an acoustic coupling medium. In some embodiments, an acoustic coupling medium, such as an acoustic coupling gel or an acoustic coupling cream, can comprise the medicant. In some embodiments, a medicant is administered to a skin surface above the ROI. In some applications, the medicant can be the acoustic coupling medium. In some applications, the medicant can be a combination of medicants, such as combinations of those described herein.

A medicant can comprise an anesthetic. In some aspects, the anesthetic can comprise lidocaine, benzocaine, prilocaine, tetracaine, novocain, butamben, dibucaine, oxybuprocaine, pramoxine, proparacaine, proxymetacaine, tetracaine, or any combination thereof. The anesthetic an eliminate or reduce the pain generated by the application of ultrasound energy to the skin, for example, the creation of the microchannels in the skin by ultrasound energy. The anesthetic can constrict blood flow, which can eliminate or reduce blood flowing that emerges to the skin surface by way of damage from the application of ultrasound energy to the skin, for example, blood flowing up a micro-channel generated by ultrasound energy and onto the skin surface. Further, the use of an anesthetic, such as lidocaine, in the acoustic coupling medium substantially eliminates skin irritation from the application of ultrasound energy, such as the ultrasound-induced creation of micro-channels penetrating the skin surface.

A medicant can comprise a drug, a vaccine, a nutraceatical, or an active ingredient. A medicant can comprise blood or a blood component, an allergenic, a somatic cell, a recombinant therapeutic protein, or other living cells that are used as therapeutics to treat diseases or as actives to produce a cosmetic or a medical effect. A medicant can comprise a biologic, such as for example a recombinant DNA therapy, synthetic growth hormone, monoclonal antibodies, or receptor constructs. A medicant can comprise stem cells.

A medicant can comprise adsorbent chemicals, such as zeolites, and other hemostatic agents are used in sealing severe injuries quickly. A medicant can comprise thrombin and/or fibrin glue, which can be used surgically to treat bleeding and to thrombose aneurysms. A medicant can comprise Desmopressin, which can be used to improve platelet function by activating arginine vasopressin receptor 1A. A medicant can comprise a coagulation factor concentrates, which can be used to treat hemophilia, to reverse the effects of anticoagulants, and to treat bleeding in patients with impaired coagulation factor synthesis or increased consumption. A medicant can comprise a Prothrombin complex concentrate, cryoprecipitate and fresh frozen plasma, which can be used as coagulation factor products. A medicant can comprise recombinant activated human factor VII, which can be used in the treatment of major bleeding. A medicant can comprise tranexamic acid and/or aminocaproic acid, which can inhibit fibrinolysis, and lead to a de facto reduced bleeding rate. A medicant can comprise platelet-rich plasma (PRP), mesenchymal stem cells, or growth factors. For example, PRP is typically a fraction of blood that has been centrifuged. The PRP is then used for stimulating healing of the injury. The PRP typically contains thrombocytes (platelets) and cytokines (growth factors). The PRP may also contain thrombin and may contain fibenogen, which when combined can form fibrin glue.

In addition, a medicant can comprise a steroid, such as, for example, like the glucocorticoid cortisol. A medicant can comprise an active compound, such as, for example, alpha lipoic Acid, DMAE, vitamin C ester, tocotrienols, and/or phospholipids. A medicant can comprise a pharmaceutical compound such as for example, cortisone, Etanercept, Abatacept, Adalimumab, or Infliximab. A medicant can comprise Botox. A medicant can comprise lignin peroxidase, which can be derived from fungus and can be used for skin lightening applications. A medicant can comprise hydrogen peroxide, which can be used for skin lighting applications.

The medicant can comprise an anti-inflammatory agent, such as, for example, a non-steroidal anti-inflammatory drug (NSAID), such as aspirin, celecoxib (Celebrex), diclofenac (Voltaren), diflunisal (Dolobid), etodolac (Lodine), ibuprofen (Motrin), indomethacin (Indocin), ketoprofen (Orudis), ketorolac (Toradol), nabumetone (Relafen), naproxen (Aleve, Naprosyn), oxaprozin (Daypro), piroxicam (Feldene), salsalate (Amigesic), sulindac (Clinoril), or tolmetin (Tolectin).

Still further, a medicant can comprise an active ingredient which provides a cosmetic and/or therapeutic effect to the area of application on the skin. Such active ingredients can include skin lightening agents, anti-acne agents, emollients, non-steroidal anti-inflammatory agents, topical anesthetics, artificial tanning agents, antiseptics, anti-microbial and anti-fungal actives, skin soothing agents, sunscreen agents, skin barrier repair agents, anti-wrinkle agents, anti-skin atrophy actives, lipids, sebum inhibitors, sebum inhibitors, skin sensates, protease inhibitors, skin tightening agents, anti-itch agents, hair growth inhibitors, desquamation enzyme enhancers, anti-glycation agents, compounds which stimulate collagen production, and mixtures thereof.

Other examples of such active ingredients can include any of panthenol, tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate), azelaic acid, arachidonic acid, tetracycline, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

A medicant can be a natural or synthetic compound or a combination of compounds, or a drug, or a biologic, as described herein, or is known to one skilled in the art, or is developed in the future.

A medicant can be diluted with an appropriate solvent for delivery. For example, a medicant can be diluted or mixed with a solvent to lower viscosity to improve transfer of the medicant. For example, a medicant can be diluted or mixed with a solvent that is a vehicle for transfer of the medicant, such as, for example, mixing a medicant with a formulation of polyethylene glycol (PEG). In some applications, the medicant can be mixed with a solvent to improve a tissue effect, such as uptake into the tissue, such as, for example, mixing a medicant with dimethyl sulfoxide (DMSO). In some applications, the medicant can be mixed with a solvent, which can restrict or inhibit an ultrasound energy effect. For example, a medicant can be mixed with ethanol (EtOH), which inhibits the thermal effect of ablation. In some applications, the medicant can be mixed with a solvent, which can amplify an ultrasound energy effect. For example, a medicant can be mixed with a contrast agent, which can be configured to promote higher attenuation and/or cavitation at lower acoustic pressures.

A medicant can be in a non-liquid state. In some applications, a medicant can be a gel or a solid, which by using a thermal effect, can melt into a liquid state suitable for delivery. For example, a medicant can be mixed into a thermally responsive hydrogel, which is configured to transform into an injectable state upon receiving a suitable amount of thermal energy emitted from a transducer.

In some aspects, a medicant can be administered to a skin surface above the ROI. The medicant can be mixed into or be a component of an acoustic coupling medium. In some applications, the medicant can be the acoustic coupling medium. In some aspects, the acoustic coupling medium can comprise a preservative and/or a preservative enhancer, such as, for example, water-soluble or solubilizable preservatives including Germall 115, methyl, ethyl, propyl and butyl esters of hydroxybenzoic acid, benzyl alcohol, sodium metabisulfite, imidazolidinyl urea, EDTA and its salts, Bronopol (2-bromo-2-nitropropane- -1,3-diol) and phenoxypropanol; antifoaming agents; binders; biological additives; bulking agents; coloring agents; perfumes, essential oils, and other natural extracts.

In general, the microneedles 14 described herein can be solid or hollow. The microneedle 14 can have a length ranging from 200 μm to 2.5 mm. The microneedles 14 can be arranged in an array having a microneedle concentration ranging from 10 microneedles per $cm^2$ to 1000 microneedles per $cm^2$. The microneedle can have a diameter of 25 gauge or smaller (i.e. a higher gauge value), including but not limited to, 27 gauge or smaller, 30 gauge or smaller, or a diameter in the range of 25 gauge to 35 gauge. The microneedle 14 can have a substantially consistent diameter along their length or can have a diameter that varies along their length. In certain aspects, the microneedle 14 can have a diameter that tapers to form a point at a tip of the microneedle 14. In some aspects, the microneedle can have a diameter, length, or both sufficiently small to prevent pain for being registered in a patient or to prevent bleeding within a patient upon insertion into the patient's skin.

In certain aspects, the ultrasound energy fields described herein can be coupled into the microneedles 14. This can cause a vibration in the microneedles 14 that can be sensed by a patient if the ultrasound energy field has a low enough frequency. This can also cause a thermal effect in the microneedles 14 if the ultrasound energy field is configured to produce a thermal effect. These effects can relieve pain or assist in healing.

In certain aspects, the delivery system 10 can be configured as a transdermal patch. For example, the delivery system 10 can be configured for off-the-shelf operation, where the delivery system 10 include the medicant in appropriate dosage within the standoff 52 and a suitable portable power supply, such as battery power, to power the delivery system 10. After removing any packaging for the delivery system 10, the delivery system 10 can be applied to a location by a patient or a user. In certain aspects, the delivery system 10 can include an adhesive material on the bottom surface of the standoff 52 or a patch that extends over the delivery system 10 to facilitate retention of coupling between the delivery system 10 and the skin surface.

In certain aspects, the delivery system 10 can have an on-off switch or a separate on-off device that allows a patient or user to turn the delivery system 10 on (and subsequently off) when the delivery system 10 is properly located on the skin surface. The delivery system 10 can utilize at least one ultrasound energy effect to move the medicant from the standoff 52 to below the skin surface.

A delivery system 10 as described herein can have significant advantages over a traditional transdermal patch. For example, the delivery system 10 can deliver medicants having a higher molecular weight, for example, medicants having a molecular weight of at least about 100 Da or at least about 500 Da. As another example, the delivery system 10 does not rely on mechanical diffusion, so lower doses of the medicant can be deployed because more of the medicant reaches areas beneath the skin surface. As yet another example, the delivery system 10 is not limited to deploying medicants having an affinity for both lipophilic and hydrophilic phases or medicants that are non-ionic. In certain aspects, the delivery system 10 can include a solar panel, which can optionally be no bigger than the area of a patch covering the delivery system 10, to supplement power to the delivery system 10.

In certain aspects, the microneedles 14 can be retracted inside the delivery system 10. Once the delivery system 10 has been positioned, the microneedles 14 can be extended to puncture the membrane 18. Once the membrane 18 has been punctured, the microneedles 14 can optionally be retracted again.

The membrane 18 can have a thickness ranging from 1 μm to 2.5 mm, including but not limited to, a thickness ranging from 2 μm to 1 mm, from 5 μm to 100 μm, from 10 μm to 40 µm, or other combinations of the lower and upper limits of these ranges not explicitly recited.

In certain aspects, the microchannels 42 can have a diameter ranging from 50 µm to 1 mm. The microchannels 42 can have a depth ranging from 50 µm to 3 mm.

The photon source 72 can be a laser, a light-emitting diode ("LED"), an intense pulsed light source, or a combination thereof. In certain aspect, the photon source 72 can be an Er:YAG laser emitting light at 2940 nm, a $CO_2$ laser emitting light at 10.66 µm, a nanosecond Q-switched laser, a picosecond laser, a femtosecond laser, or other light source that a person having ordinary skill in the art would identify as capable of initiating a photoacoustic effect or generating microchannels in the membrane 18.

The systems and methods described herein can be employed in numerous clinical applications. For example, a treatment for scars can include a medicant directed by acoustic energy through micro-channels to a scar location. A second acoustic energy can be directed to the scar location and be configured to interact with the medicant to remodel and/or modify the scar tissue and eventually replace the scar tissue via remodeling. The treatment can also include directing therapeutic acoustic energy into the scar tissue. In some applications, the therapeutic acoustic energy can be configured to ablate a portion of the scar tissue, thereby removing a portion of the scar tissue. In some applications, the therapeutic acoustic energy can be configured to create a lesion in or near the scar tissue, thereby facilitating skin tightening above the lesion. In some applications, the therapeutic acoustic energy can be configured to remodel and/or increase an amount of collagen around the scar tissue, thereby replacing portions of the scar tissue with newly formed collagen.

In another example, the systems and methods described herein can be used in the treatment of hyperpigmentation. A medicant can be a skin lightening agent, which can be an active ingredient that improves hyperpigmentation. Without being bound by theory, use of skin lightening agents can effectively stimulate the epidermis, particularly the melanocyte region, where the melanin is generated. The combined use of the skin lightening agent and ultrasound energy can provide synergistic skin lightening benefit. A medicant comprise a skin lightening agent, such as, for example, ascorbic acid compounds, vitamin B3 compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents can be advantageous as they may provide skin lightening benefit through different mechanisms.

In one aspect, a combination of ascorbic acid compounds and vitamin B3 compounds can be used. Examples of ascorbic acid compounds can include L-ascorbic acid, ascorbic acid salt, and derivatives thereof. Examples of ascorbic acid salts include sodium, potassium, lithium, calcium, magnesium, barium, ammonium and protamine salts. Examples of ascorbic acid derivatives include for example, esters of ascorbic acid, and ester salts of ascorbic acid. Examples of ascorbic acid compounds include 2-O-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. In addition, medicant can comprise lignin peroxidase, which can be derived from fungus used for skin lightening applications. In another example, medicant can comprise hydrogen peroxide, which can be used for skin lighting applications.

In an exemplary application, a coupling agent can comprise a medicant, which comprises a skin lighting agent. Ultrasound energy can direct the lightening agent into the epidermis and into contact with melanin. The lightening agent can remove excess melanin. Additional ultrasound energy can be directed to the epidermis to provide a cavitation effect to break up the excess melanin pigment. In some examples, additional ultrasound energy can be directed to the epidermis to provide a thermal effect, which can be configured to increase the effectiveness of the skin lightening agent. In one example, the skin lightening agent can be hydrogen peroxide and the ultrasound energy can increase the temperature of the hydrogen peroxide by at least 1° C. and to about 15° C., which increases the effectiveness of the skin lightening agent.

In another example of a clinical application, the systems and methods described herein can be used in the treatment of hypopigmentation. In an exemplary application, a coupling agent can comprise a medicant, which can comprise a corticosteroid. Ultrasound energy can direct the corticosteroid into the epidermis at the light colored areas of the skin. A second ultrasound energy can be directed to the treatment location and be configured to interact with the corticosteroid to provide a synergistic treatment to increase pigment concentration at the treatment location. A second energy, such as, a photon-based energy from a laser can be directed to the treatment location to further increase the pigment concentration in the treatment location. A third energy, such as, ultrasound energy can be directed to the treatment location to disperse the generated pigment and provide an even coloring pattern at the treatment location.

In another example, large molecule medicants can be delivered using the systems and methods described herein. A large molecule can be greater than 500 Da. A large molecule can be a medicinal product manufactured in or extracted from biological sources. Examples of large molecule include vaccines, blood or blood components, allergenics, somatic cells, gene therapies, tissues, recombinant therapeutic protein and living cells. In one example, a large molecule comprises stem cells. An energy effect is provided by an acoustic energy field, which is configured to drive the large molecule through the micro-channels and into subcutaneous tissue. The energy effect can be acoustic streaming and/or cavitation. In some applications, the energy effect is a thermal effect, which can be configured to lower the viscosity of a large molecule for improved transfer through the micro-channels.

In another example, chemotherapy drugs can be delivered using the systems and methods described herein. Some of the advantages, of using such systems and methods, include concentrating the chemotherapy drug to the tumor site (as opposed to exposing the whole body to the drug), lower doses may be required (due to the site specific treatment), and greater effectiveness of the drug.

In some applications, a chemotherapy drug can be a large molecule. In some applications, the systems and methods, described herein, can deliver anti-body drug conjugates, which target cancer stem cells to destroy a tumor. In some applications, a chemotherapy drug is a liposome encapsulated chemotherapy drug, which can be delivered through the micro-channels to a treatment site by an acoustic energy field, and then a second acoustic energy field can be delivered to melt the liposome and release the chemotherapy drug. In some applications, an acoustic energy field can be delivered, which is configured to provide micro-bubbles (cavitation) to a tumor in a treatment site without generating heat, which can lead to reduction or elimination of the tumor. These micro-bubbles can increase microvessel permeability of drugs, enhance drug penetration through the interstitial space, and increase tumor cell uptake of the drugs, thus enhancing the antitumor effectiveness of the drugs.

In some applications of chemotherapy, a drug-loaded nanoemulsion can be driven through the micro-channels to a tumor site via an acoustic energy field. A second acoustic energy field can be delivered to the tumor site and can be configured to trigger drug release from nanodroplets, which can be created by micro-bubbles. A third acoustic energy field can be delivered to the tumor site and can be configured to produce an energy effect, for example, a thermal effect and/or cavitation, which enhances uptake of the drug by the tumor.

In another example, photodynamic therapy can be delivered using the systems and methods described herein. As known to one skilled in the art, photodynamic therapy is a medical treatment that utilizes a medicant, which comprises a photosensitizing agent and a photon-emission source to activate the administered medicant. In some applications, the medicant comprising a photosensitizing agent is delivered through the micro-channels into tissue via an acoustic energy field. After the medicant has been delivered, a second acoustic energy field can be delivered to enhance permeability and/or uptake of the medicant by the tissue. After the medicant has been delivered, a photon energy field at a specific wavelength is delivered from the photon-emission source to the tissue, which activates the medicant. The photon-emission source can include, but are not limited to: laser, LED or intense pulsed light. The optimal photon-emission source is determined by the ideal wavelength for activation of the medicant and the location of the target tissue. The photon energy field is directly applied to the target tissue for a specific amount of time. The medicant can be Levulan, which is used for the treatment of skin cancer. The medicant can be Metvix, which is used for the treatment of skin cancer. The medicant can be Photofin, which is used for the treatment of bladder cancer, lung cancer and esophagus cancer. The medicant can be aminolevulinic acid, which has been used in the treatment of various skin conditions, such as, for example, acne, rosacea, sun damage, enlarged sebaceous glands, wrinkles, warts, hidradenitis suppurativa, and psoriasis.

In another example, injuries to muscles can be treated using the systems and methods described herein. For treating an injury to a muscle, ligament, or tendon, a medicant can comprise platelet-rich plasma (PRP), mesenchymal stem cells, or growth factors. For example, PRP is typically a fraction of blood that has been centrifuged. The PRP is then used for stimulating healing of the injury. The PRP typically contains thrombocytes (platelets) and cytokines (growth factors). The PRP may also contain thrombin and may contain fibenogen, which when combined can form fibrin glue. The medicant can be directed through a micro-channels to the injury, such as, for example a tear in the tissue. An acoustic energy field can then be directed to the injury to activate the medicant and/or disperse the medicant. The acoustic energy field can create a thermal effect to heat the injury location which can initiate interaction of the medicant with the tissue at the injury location and/or increase blood perfusion in the injury location. The acoustic energy field can ablate a portion of tissue in the injury location, which can peak inflammation and increase the speed of the healing process. The acoustic energy field can be directed to the injury location and weld together the tear using both an ablative thermal effect and various mechanical effects.

In an example, acne can be treated using the systems and methods described herein. A medicant can comprise any one or more of cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline. The medicant is directed through the micro-channels to a ROI comprising a sebaceous gland. The medicant interacts with bacteria in the sebaceous gland to reduce or eliminate the bacteria responsible for acne. An acoustic energy field can provide a mechanical effect to disperse the medicant into one or more sebaceous gland. An acoustic energy field can provide a thermal effect to accelerate the reaction of the medicant to eliminate or reduce the amount of bacteria in the sebaceous gland. An acoustic energy field can provide a thermal effect to injure or destroy at least a portion of the sebaceous gland. A photon based energy field can be directed to the medicant in the ROI to initiate a photodymanic effect to activate the medicant. A photon based energy field can be directed to the medicant in the ROI to reduce photosensitivity of the tissue in the ROI from sunlight.

As used herein, pulse width is the time from the start of the pulse to the end of the pulse measured at a −3 dB or −6 dB power point.

As used herein, "acoustic streaming" refers to a force of acoustic energy which displaces a material through a tissue environment.

Example 1

Several water baths were each covered by a membrane 18 with the membrane 18 contacting the water within the water bath. A first water bath was covered by a 0.8 mm thick silicon rubber membrane 18 having microchannels with a diameter of 160 μm. Second and third water baths were covered by a 0.8 mm thick silicon rubber membrane 18 having microchannels with a diameter of 100 microns. A fourth water bath was covered by a 0.8 mm thick high-attenuation FR-4 membrane 18 having microchannels with a diameter of 40 microns. Fifth and sixth water baths were covered by an approximately 1 mm thick ex vivo pig skin membrane 18 having microchannels with a diameter of 70-100 microns. Dyed glycerin solutions having viscosities of 400-612 centipoise served as the transport target 40 and were applied to the surface of each membrane 18. Without application of ultrasound, no glycerin solution passed through the microchannels.

Figure 9A:
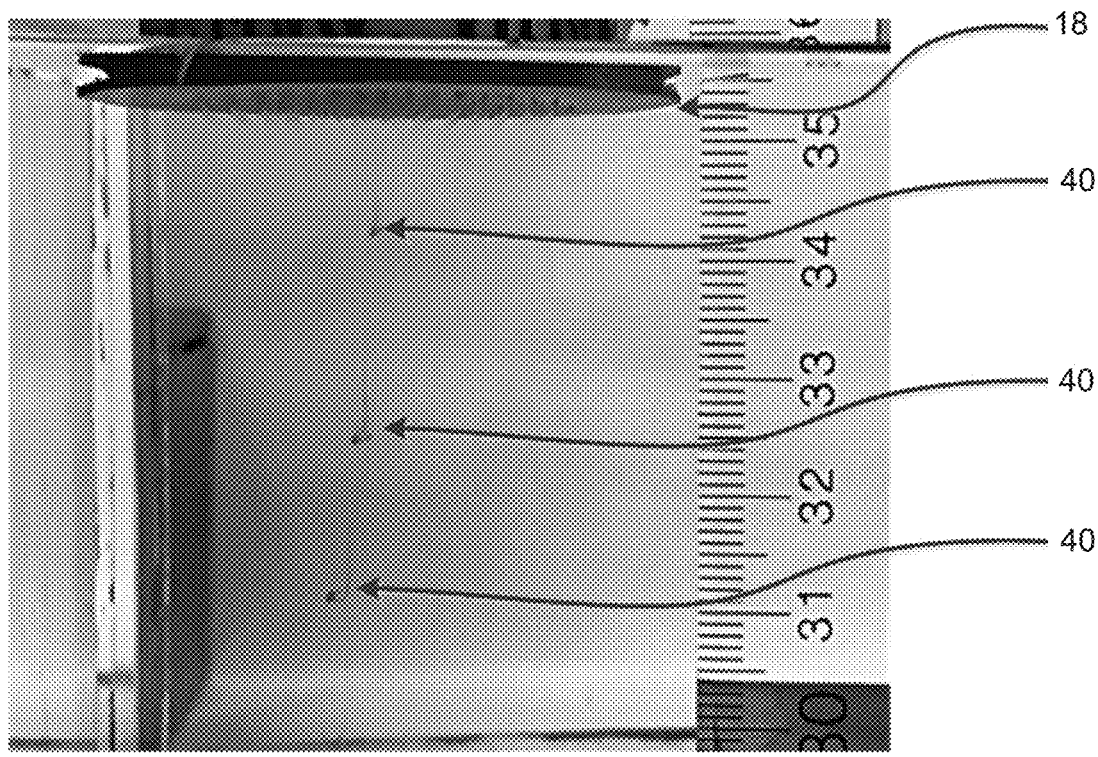
FIG. 9A is a picture showing glycerin driven through microchannels in a membrane as shown in Example 2, according to one aspect of the present disclosure.
Figure 9B:
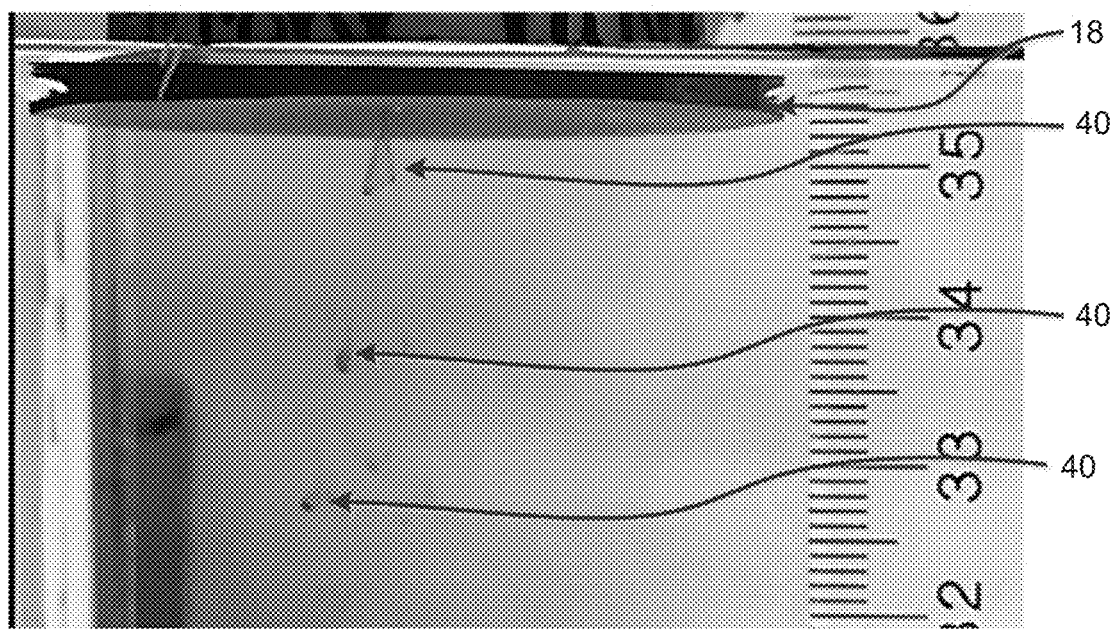
FIG. 9B is a picture showing glycerin driven through microchannels in a membrane as shown in Example 2, according to one aspect of the present disclosure.

Referring to FIGS. 9A and 9B, for each of the first and second water baths, a 2 cm diameter transducer was coupled to the glycerin and an ultrasound energy field having a frequency of 3.3 MHz, a peak power of 1 kW, a pulse width of 121 ms, and a pulse repetition rate of 2.5 Hz was focused to a depth just beneath the membrane. The peak intensity was about 4 kW/cm$^2$. The acoustic pressure was estimated to be about 10 MPa. The glycerin was driven through the microchannel, across the membrane 18, and into the water.

Figure 9C:
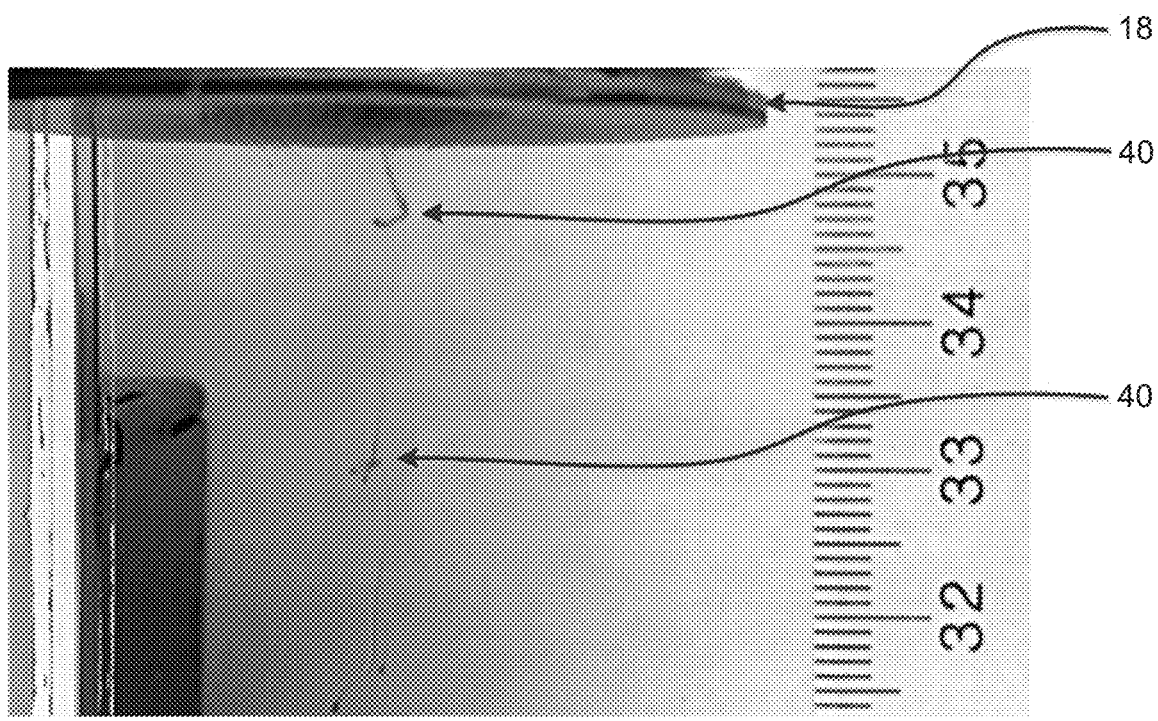
FIG. 9C is a picture showing glycerin driven through microchannels in a membrane as shown in Example 2, according to one aspect of the present disclosure.

Referring to FIG. 9C, for the third water bath, a 2 cm diameter transducer was coupled to the glycerin and an ultrasound energy field having a frequency of 5 MHz, a peak power of 1 kW, a pulse width of 121 ms, and a pulse repetition rate of 2.5 Hz was focused to a depth just beneath the membrane. The peak intensity was about 8 kW/cm². The acoustic pressure was estimated to be about 20 MPa. The glycerin was driven through the microchannel, across the membrane 18, and into the water.

Figure 9D:
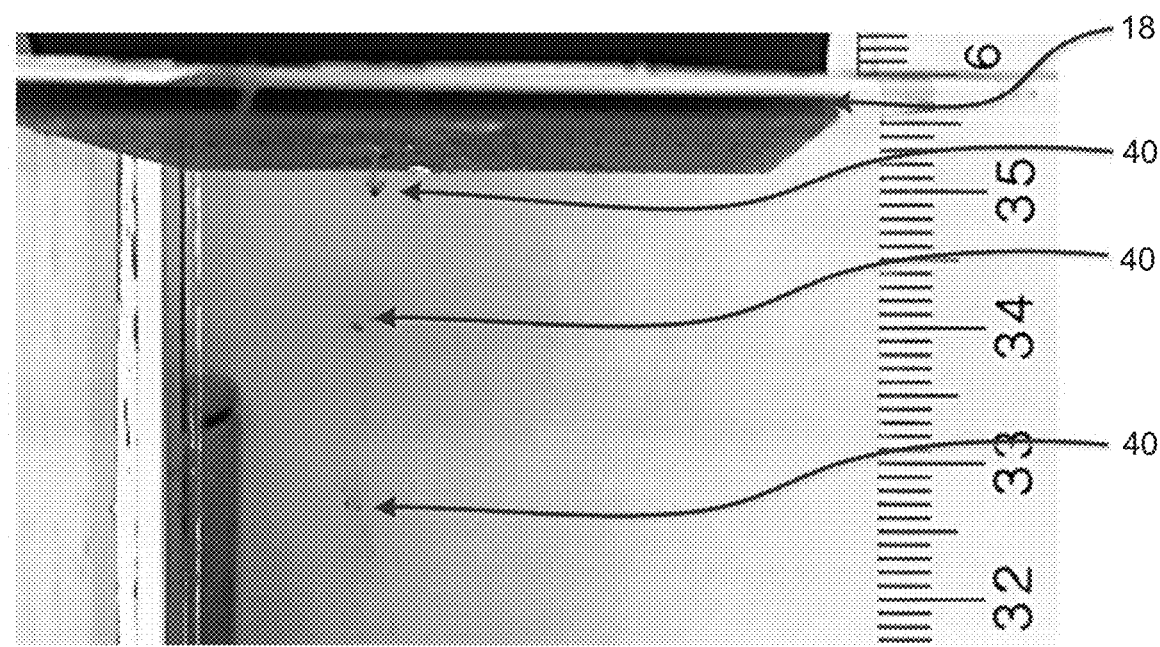
FIG. 9D is a picture showing glycerin driven through microchannels in a membrane as shown in Example 2, according to one aspect of the present disclosure.

Referring to FIG. 9D, for the fourth water bath, a 2 cm diameter transducer was coupled to the glycerin and an ultrasound energy field having a frequency of 5 MHz, a peak power of 1 kW, a pulse width of 121 ms, and a pulse repetition rate of 2.5 Hz was focused to a depth just beneath the membrane. The peak intensity was about 8 kW/cm². The acoustic pressure was estimated to be about 15 MPa. The glycerin was driven through the microchannel, across the membrane 18, and into the water.

For the fifth water bath, a 2 cm diameter transducer was coupled to the glycerin and an ultrasound energy field having the same properties as described above with respect to the examples shown in FIGS. 9A and 9B was focused to a depth just beneath the membrane. For the sixth water bath, a 2 cm diameter transducer was coupled to the glycerin and an ultrasound energy field having the same properties as described above with respect to the examples shown in FIGS. 9C and 9D was focused to a depth just beneath the membrane. In both cases, the glycerin was driven through the microchannel, across the membrane, and into the water.

Measured linear streaming velocities for the above-referenced examples ranged from 24 mm/s to 480 mm/s. As should be appreciated, in FIGS. 9A, 9B, 9C, and 9D, drops that are spaced further apart are indicative of a greater linear streaming velocity.

Additional membrane parameters and ultrasound parameters were also deployed in the same general experimental setup as described above. Linear streaming velocities were measured up to 1.5 m/s.

The present disclosure has been described above with reference to various exemplary configurations. However, those skilled in the art will recognize that changes and modifications may be made to the exemplary configurations without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound treatment as described above is suitable for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitable placement for the transducer. Moreover, while the various exemplary embodiments may comprise non-invasive configurations, system can also be configured for at least some level of invasive treatment application. These and other changes or modifications are intended to be included within the scope of the present invention, as set forth in the following claims.

The invention claimed is:

1. A method for transporting a medicant across a stratum corneum layer of a skin and into a dermis layer of the skin, the method comprising:
   a) contacting a top surface of the stratum corneum layer with the medicant;
   b) creating a microchannel in the stratum corneum layer, the microchannel providing fluid communication between the top surface of the stratum corneum layer and an epidermis layer of the skin;
   c) after creating the microchannel, directing a first acoustic energy field from an acoustic energy source or a first photon-based energy field from a photon-based energy source to the medicant, thereby driving the medicant through the microchannel and into the epidermis layer of the skin, the first acoustic energy field is a pulsed first acoustic energy, has a pulse width of 33 nanoseconds to 5 seconds, a frequency of 1 MHz to 30 MHz, and a peak intensity of 5 W/cm² to 70 kW/cm², and generates a pressure of 10 kPa to 100 MPa, thereby initiating acoustic streaming or inertial cavitation that drives the medicant through the microchannel and into the epidermis layer of the skin; and
   d) subsequent to the medicant being driven into the epidermis layer of the skin, applying a second acoustic energy field to the medicant, thereby driving the medicant from the epidermis layer of the skin and into the dermis layer of the skin wherein step b) includes puncturing the stratum corneum layer with a microneedle to create the microchannel in the stratum corneum layer.

2. The method according to claim 1, wherein step c) comprises directing the first acoustic energy field from the acoustic energy source to the medicant.

3. The method according to claim 1, wherein the pulsed first acoustic energy is applied for more than one pulse and pulses are separated by a length of time of 10 microseconds to 1 second.

4. The method according to claim 1, wherein step b) includes directing a second photon-based energy field from a remote microchannel probe into the stratum corneum layer.

5. The method according to claim 1, wherein step b) includes rolling a cylinder having an outer surface comprising a plurality of microneedles on the top surface of the stratum corneum layer, thereby creating a plurality of microchannels in the stratum corneum layer.

6. The method according to claim 1, wherein the microchannel has a diameter ranging from 50 μm to 3 mm.

7. A method for transporting a transport target across a membrane that is semi-permeable or impermeable to a transport target, the method comprising:
   a) contacting a top surface of the membrane with the transport target;
   b) creating a microchannel in the membrane, the membrane having a top membrane surface and a bottom membrane surface, the microchannel providing fluid communication between the top membrane surface and a first material layer contacting the bottom membrane surface; and
   c) after creating the microchannel, directing a first acoustic energy field from an acoustic energy source or a first photon-based energy field from a photon-based energy source to the transport target, thereby driving the transport target through the microchannel and into the first material layer, and
   wherein the first acoustic energy field is a pulsed first acoustic energy, has a pulse width of 33 nanoseconds to 5 seconds, a frequency of 1 MHz to 30 MHz, and a peak intensity of 5 W/cm2 to 70 kW/cm2, and generates a pressure of 10 kPa to 100 MPa, thereby initiating acoustic streaming or inertial cavitation that drives the transport target through the microchannel and into the first material layer wherein step b) includes puncturing the stratum corneum layer with a microneedle to create the microchannel in the stratum corneum layer.

8. The method according to claim 7, wherein the microchannel has a diameter ranging from 50 µm to 3 mm.

9. The method according to claim 7, the method further comprising:
   d) subsequent to the transport target being driven into the first material layer, applying a second acoustic energy field to the transport target, thereby driving the transport target from the first material layer into a second material layer adjacent to the first material layer and opposite the membrane.

10. The method according to claim 7, wherein step c) comprises directing the first acoustic energy field from the acoustic energy source to the transport target.

11. The method according to claim 7, wherein the pulsed first acoustic energy is applied for more than one pulse and the pulses are separated by a length of time of 10 microseconds to 1 second.

12. The method according to claim 7, wherein step b) includes directing a second photon-based energy field from a remote microchannel probe into the membrane.

13. The method according to claim 7, wherein step b) include rolling a cylinder having an outer surface comprising a plurality of microneedles on the top membrane surface, thereby creating a plurality of microchannels in the membrane.

14. The method according to claim 7, wherein the transport target is glycerin.

* * * * *

UNITED STATES PATENT AND TRADEMARK OFFICE
CERTIFICATE OF CORRECTION

| | |
|---|---|
| PATENT NO. | : 10,765,851 B2 |
| APPLICATION NO. | : 15/059773 |
| DATED | : September 8, 2020 |
| INVENTOR(S) | : Michael H. Slayton |

It is certified that error appears in the above-identified patent and that said Letters Patent is hereby corrected as shown below:

In the Specification

Column 5, Line 35, "delivery can" should be --delivery system 10 can--.

Signed and Sealed this
Seventh Day of June, 2022

Katherine Kelly Vidal
*Director of the United States Patent and Trademark Office*